(12) United States Patent
Sampson et al.

(10) Patent No.: US 10,058,321 B2
(45) Date of Patent: Aug. 28, 2018

(54) DEVICES AND METHODS OF VISUALIZING AND DETERMINING DEPTH OF PENETRATION IN CARDIAC TISSUE

(71) Applicant: Ancora Heart, Inc., Santa Clara, CA (US)

(72) Inventors: Russel Sampson, Palo Alto, CA (US); Charles Adam, San Jose, CA (US); Son Nguyen, San Jose, CA (US); David Scott Baron, Sunnyvale, CA (US)

(73) Assignee: Ancora Heart, Inc., Santa Clara, CA (US)

( * ) Notice: Subject to any disclaimer, the term of this patent is extended or adjusted under 35 U.S.C. 154(b) by 0 days.

(21) Appl. No.: 15/061,748

(22) Filed: Mar. 4, 2016

(65) Prior Publication Data

US 2016/0256149 A1 Sep. 8, 2016

Related U.S. Application Data

(60) Provisional application No. 62/128,628, filed on Mar. 5, 2015.

(51) Int. Cl.
*A61B 17/10* (2006.01)
*A61B 17/04* (2006.01)
(Continued)

(52) U.S. Cl.
CPC ...... *A61B 17/0401* (2013.01); *A61B 17/0469* (2013.01); *A61B 17/0493* (2013.01);
(Continued)

(58) Field of Classification Search
CPC ............ A61B 17/0401; A61B 17/0469; A61B 17/0493; A61B 2017/00247;
(Continued)

(56) References Cited

U.S. PATENT DOCUMENTS 3,656,185 A 4/1972 Carpentier
3,773,034 A 11/1973 Burns et al.
(Continued)

FOREIGN PATENT DOCUMENTS

EP 0 637 431 A1 2/1995
EP 0 669 101 A1 8/1995
(Continued)

OTHER PUBLICATIONS

Final Office Action dated May 12, 2010, for U.S. Appl. No. 11/583,627, filed Oct. 18, 2006, 18 pages.
(Continued)

*Primary Examiner* — Elizabeth Houston
*Assistant Examiner* — Mohamed Gabr
(74) *Attorney, Agent, or Firm* — Cooley LLP

(57) ABSTRACT

Disclosed herein are devices and methods for assessing the surface of a target cardiac tissue and for delivering a tissue anchor to cardiac tissue at a preselected depth within the myocardium in a beating heart procedure. In one variation, an anchor delivery device comprises an elongate body, a tissue anchor disposed within a first longitudinal lumen of the elongate body, and a tissue depth indicator slidable within a second longitudinal lumen of the elongate body. The tissue depth indicator has a first configuration that indicates the boundary of the surface of the target tissue and a second configuration that indicates when the distal tip of the elongate body has been advanced to a preselected depth into the target tissue. In some variations, a tissue depth indicator may also be configured to resist or limit the penetration of the delivery device into tissue after a preselected depth has been reached.

14 Claims, 23 Drawing Sheets

(51) Int. Cl.
*A61B 90/00* (2016.01)
*A61B 17/00* (2006.01)

(52) U.S. Cl.
CPC .... *A61B 90/06* (2016.02); *A61B 2017/00247* (2013.01); *A61B 2017/00336* (2013.01); *A61B 2017/0409* (2013.01); *A61B 2017/0441* (2013.01); *A61B 2017/0464* (2013.01); *A61B 2090/062* (2016.02); *A61B 2090/0811* (2016.02); *A61B 2090/3966* (2016.02)

(58) Field of Classification Search
CPC .. A61B 2017/00336; A61B 2017/0409; A61B 2017/0441; A61B 2017/0464; A61B 2090/062; A61B 2090/0811; A61B 2090/3966; A61B 90/06
USPC ...................................................... 606/142
See application file for complete search history.

(56) References Cited

U.S. PATENT DOCUMENTS

| | | |
|---|---|---|
| 3,961,419 A | 6/1976 | Schwartz |
| 3,976,079 A | 8/1976 | Samuels et al. |
| 4,014,492 A | 3/1977 | Rothfuss |
| 4,034,473 A | 7/1977 | May |
| 4,042,979 A | 8/1977 | Angell |
| 4,043,504 A | 8/1977 | Hueil et al. |
| 4,053,979 A | 10/1977 | Tuthill et al. |
| 4,055,861 A | 11/1977 | Carpentier et al. |
| 4,069,825 A | 1/1978 | Akiyama |
| 4,273,127 A | 6/1981 | Auth et al. |
| 4,290,151 A | 9/1981 | Massana |
| 4,384,406 A | 5/1983 | Tischlinger |
| 4,445,509 A | 5/1984 | Auth |
| 4,445,892 A | 5/1984 | Hussein et al. |
| 4,489,446 A | 12/1984 | Reed |
| 4,494,542 A | 1/1985 | Lee |
| 4,619,247 A | 10/1986 | Inoue et al. |
| 4,681,093 A | 7/1987 | Ono et al. |
| 4,700,250 A | 10/1987 | Kuriyama |
| 4,726,371 A | 2/1988 | Gibbens |
| 4,758,221 A | 7/1988 | Jureidini |
| 4,784,133 A | 11/1988 | Mackin |
| 4,845,851 A | 7/1989 | Warthen |
| 4,848,341 A | 7/1989 | Ahmad |
| 4,850,354 A | 7/1989 | McGurk-Burleson et al. |
| 4,961,738 A | 10/1990 | Mackin |
| 4,969,893 A | 11/1990 | Swor |
| 4,976,710 A | 12/1990 | Mackin |
| 5,053,047 A | 10/1991 | Yoon |
| 5,064,431 A | 11/1991 | Gilbertson et al. |
| 5,084,058 A | 1/1992 | Li |
| 5,103,804 A | 4/1992 | Abele et al. |
| 5,133,723 A | 7/1992 | Li et al. |
| 5,195,990 A | 5/1993 | Weldon |
| 5,221,255 A | 6/1993 | Mahurkar et al. |
| 5,242,456 A | 9/1993 | Nash et al. |
| 5,242,457 A | 9/1993 | Akopov et al. |
| 5,257,975 A | 11/1993 | Foshee |
| 5,312,341 A | 5/1994 | Turi |
| 5,314,407 A | 5/1994 | Auth et al. |
| 5,324,298 A | 6/1994 | Phillips et al. |
| 5,344,439 A | 9/1994 | Otten |
| 5,346,500 A | 9/1994 | Suchart |
| 5,358,479 A | 10/1994 | Wilson |
| 5,364,407 A | 11/1994 | Poll |
| 5,366,479 A | 11/1994 | McGarry et al. |
| 5,368,564 A | 11/1994 | Savage |
| 5,368,591 A | 11/1994 | Lennox et al. |
| 5,383,905 A | 1/1995 | Golds et al. |
| 5,403,348 A | 4/1995 | Bonutti |
| 5,409,483 A | 4/1995 | Campbell et al. |
| 5,415,666 A | 5/1995 | Gourlay et al. |
| 5,417,700 A | 5/1995 | Egan |
| 5,423,837 A | 6/1995 | Mericle et al. |
| 5,437,680 A | 8/1995 | Yoon |
| 5,439,470 A | 8/1995 | Li |
| 5,450,860 A | 9/1995 | O'Connor |
| 5,452,513 A | 9/1995 | Zinnbauer et al. |
| 5,474,572 A | 12/1995 | Hayhurst |
| 5,507,725 A | 4/1996 | Savage et al. |
| 5,520,702 A | 5/1996 | Sauer et al. |
| 5,522,873 A | 6/1996 | Jackman et al. |
| 5,524,630 A | 6/1996 | Crowley |
| 5,527,323 A | 6/1996 | Jervis et al. |
| 5,545,134 A | 8/1996 | Hilaire et al. |
| 5,545,168 A | 8/1996 | Burke |
| 5,565,122 A | 10/1996 | Zinnbauer et al. |
| 5,571,215 A | 11/1996 | Sterman et al. |
| 5,591,194 A | 1/1997 | Berthiaume |
| 5,626,614 A | 5/1997 | Hart |
| 5,630,824 A | 5/1997 | Hart |
| 5,640,955 A | 6/1997 | Ockuly et al. |
| 5,643,289 A | 7/1997 | Sauer et al. |
| 5,669,917 A | 9/1997 | Sauer et al. |
| 5,674,279 A | 10/1997 | Wright et al. |
| 5,690,655 A | 11/1997 | Hart et al. |
| 5,695,505 A | 12/1997 | Yoon |
| 5,709,695 A | 1/1998 | Northrup, III |
| 5,713,950 A | 2/1998 | Cox |
| 5,716,370 A | 2/1998 | Williamson, IV et al. |
| 5,718,725 A | 2/1998 | Sterman et al. |
| 5,725,542 A | 3/1998 | Yoon |
| 5,735,290 A | 4/1998 | Sterman et al. |
| 5,741,260 A | 4/1998 | Songer et al. |
| 5,741,301 A | 4/1998 | Pagedas |
| 5,752,518 A | 5/1998 | McGee et al. |
| 5,752,964 A | 5/1998 | Mericle |
| 5,752,966 A | 5/1998 | Chang |
| 5,755,730 A | 5/1998 | Swain et al. |
| 5,766,189 A | 6/1998 | Matsuno |
| 5,766,240 A | 6/1998 | Johnson |
| 5,769,812 A | 6/1998 | Stevens et al. |
| 5,779,673 A | 7/1998 | Roth et al. |
| 5,779,718 A | 7/1998 | Green et al. |
| 5,807,403 A | 9/1998 | Beyar et al. |
| 5,810,848 A | 9/1998 | Hayhurst |
| 5,810,853 A | 9/1998 | Yoon |
| 5,817,107 A | 10/1998 | Schaller |
| 5,827,171 A | 10/1998 | Dobak, III et al. |
| 5,843,169 A | 12/1998 | Taheri |
| 5,848,969 A | 12/1998 | Panescu et al. |
| 5,860,992 A | 1/1999 | Daniel et al. |
| 5,860,993 A | 1/1999 | Thompson et al. |
| 5,861,003 A | 1/1999 | Latson et al. |
| 5,868,733 A | 2/1999 | Ockuly et al. |
| 5,879,371 A | 3/1999 | Gardiner et al. |
| 5,885,238 A | 3/1999 | Stevens et al. |
| 5,888,240 A | 3/1999 | Carpentier et al. |
| 5,902,321 A | 5/1999 | Caspari et al. |
| 5,904,651 A | 5/1999 | Swanson et al. |
| 5,904,657 A | 5/1999 | Unsworth et al. |
| 5,906,579 A | 5/1999 | Vander Salm et al. |
| 5,916,147 A | 6/1999 | Boury |
| 5,919,208 A | 7/1999 | Valenti |
| 5,935,149 A | 8/1999 | Ek |
| 5,947,983 A | 9/1999 | Solar et al. |
| 5,961,440 A | 10/1999 | Schweich, Jr. et al. |
| 5,961,539 A | 10/1999 | Northrup, III et al. |
| 5,972,004 A | 10/1999 | Williamson, IV et al. |
| 5,984,933 A | 11/1999 | Yoon |
| 5,989,284 A | 11/1999 | Laufer |
| 5,991,650 A | 11/1999 | Swanson et al. |
| 6,010,531 A | 1/2000 | Donlon et al. |
| 6,013,083 A | 1/2000 | Bennet |
| 6,015,428 A | 1/2000 | Pagedas |
| 6,050,936 A | 4/2000 | Schweich, Jr. et al. |
| 6,056,743 A | 5/2000 | Ellis et al. |
| 6,059,715 A | 5/2000 | Schweich, Jr. et al. |
| 6,066,160 A | 5/2000 | Colvin et al. |
| 6,074,401 A | 6/2000 | Gardiner et al. |
| 6,077,214 A | 6/2000 | Mortier et al. |
| 6,077,989 A | 6/2000 | Kandel et al. |

(56) References Cited

U.S. PATENT DOCUMENTS

| | | |
|---|---|---|
| 6,080,182 A | 6/2000 | Shaw et al. |
| 6,099,553 A | 8/2000 | Hart et al. |
| 6,110,184 A | 8/2000 | Weadock |
| 6,125,852 A | 10/2000 | Stevens et al. |
| 6,149,658 A | 11/2000 | Gardiner et al. |
| 6,156,044 A | 12/2000 | Kammerer et al. |
| 6,162,168 A | 12/2000 | Schweich, Jr. et al. |
| 6,165,183 A | 12/2000 | Kuehn et al. |
| 6,183,469 B1 | 2/2001 | Thapliyal et al. |
| 6,197,017 B1 | 3/2001 | Brock et al. |
| 6,203,531 B1 | 3/2001 | Ockuly et al. |
| 6,210,432 B1 | 4/2001 | Solem et al. |
| 6,228,096 B1 | 5/2001 | Marchand |
| 6,250,308 B1 | 6/2001 | Cox |
| 6,254,620 B1 | 7/2001 | Koh et al. |
| 6,258,118 B1 | 7/2001 | Baum et al. |
| 6,260,552 B1 | 7/2001 | Mortier et al. |
| 6,269,819 B1 | 8/2001 | Oz et al. |
| 6,283,993 B1 | 9/2001 | Cosgrove et al. |
| 6,306,149 B1 | 10/2001 | Meade |
| 6,312,447 B1 | 11/2001 | Grimes |
| 6,328,727 B1 | 12/2001 | Frazier et al. |
| 6,332,893 B1 | 12/2001 | Mortier et al. |
| 6,355,030 B1 | 3/2002 | Aldrich et al. |
| 6,378,289 B1 | 4/2002 | Trudeau et al. |
| 6,391,048 B1 | 5/2002 | Ginn et al. |
| 6,406,420 B1 | 6/2002 | McCarthy et al. |
| 6,409,743 B1 | 6/2002 | Fenton, Jr. |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,461,327 B1 | 10/2002 | Addis et al. |
| 6,491,689 B1 | 12/2002 | Ellis et al. |
| 6,514,265 B2 | 2/2003 | Ho et al. |
| 6,524,338 B1 | 2/2003 | Gundry |
| 6,533,753 B1 | 3/2003 | Haarstad et al. |
| 6,540,755 B2 | 4/2003 | Ockuly et al. |
| 6,551,332 B1 | 4/2003 | Nguyen et al. |
| 6,575,971 B2 | 6/2003 | Hauck et al. |
| 6,589,160 B2 | 7/2003 | Schweich, Jr. et al. |
| 6,602,288 B1 | 8/2003 | Cosgrove et al. |
| 6,602,289 B1 | 8/2003 | Colvin et al. |
| 6,607,541 B1 | 8/2003 | Gardiner et al. |
| 6,613,059 B2 | 9/2003 | Schaller et al. |
| 6,619,291 B2 | 9/2003 | Hlavka et al. |
| 6,626,899 B2 | 9/2003 | Houser et al. |
| 6,629,534 B1 | 10/2003 | St. Goar et al. |
| 6,641,593 B1 | 11/2003 | Schaller et al. |
| 6,648,903 B1 | 11/2003 | Pierson, III |
| 6,651,671 B1 | 11/2003 | Donlon et al. |
| 6,655,386 B1 | 12/2003 | Makower et al. |
| 6,669,687 B1 | 12/2003 | Saadat |
| 6,676,702 B2 | 1/2004 | Mathis |
| 6,689,164 B1 | 2/2004 | Seguin |
| 6,699,263 B2 | 3/2004 | Cope |
| 6,702,826 B2 | 3/2004 | Liddicoat et al. |
| 6,716,243 B1 | 4/2004 | Colvin et al. |
| 6,718,985 B2 | 4/2004 | Hlavka et al. |
| 6,723,038 B1 | 4/2004 | Schroeder et al. |
| 6,723,107 B1 | 4/2004 | Skiba et al. |
| 6,733,509 B2 | 5/2004 | Nobles et al. |
| 6,746,471 B2 | 6/2004 | Mortier et al. |
| 6,752,813 B2 | 6/2004 | Goldfarb et al. |
| 6,790,231 B2 | 9/2004 | Liddicoat et al. |
| 6,793,618 B2 | 9/2004 | Schweich, Jr. et al. |
| 6,818,001 B2 | 11/2004 | Wulfman et al. |
| 6,849,077 B2 | 2/2005 | Ricci |
| 6,908,424 B2 | 6/2005 | Mortier et al. |
| 6,923,818 B2 | 8/2005 | Muramatsu et al. |
| 6,932,792 B1 | 8/2005 | St. Goar et al. |
| 6,951,557 B2 | 10/2005 | Ellis et al. |
| 6,976,995 B2 | 12/2005 | Mathis et al. |
| 6,986,775 B2 | 1/2006 | Morales et al. |
| 6,991,643 B2 | 1/2006 | Saadat |
| 6,997,931 B2 | 2/2006 | Sauer et al. |
| 7,004,958 B2 | 2/2006 | Adams et al. |
| 7,037,334 B1 | 5/2006 | Hlavka et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,166,127 B2 | 1/2007 | Spence et al. |
| 7,186,262 B2 | 3/2007 | Saadat |
| 7,189,199 B2 | 3/2007 | McCarthy et al. |
| 7,214,230 B2 | 5/2007 | Brock et al. |
| 7,235,086 B2 | 6/2007 | Sauer et al. |
| 7,241,310 B2 | 7/2007 | Taylor et al. |
| 7,257,450 B2 | 8/2007 | Auth et al. |
| 7,326,231 B2 | 2/2008 | Phillips et al. |
| 7,331,972 B1 | 2/2008 | Cox |
| 7,344,544 B2 | 3/2008 | Bender et al. |
| 7,452,325 B2 | 11/2008 | Schaller |
| 7,534,204 B2 | 5/2009 | Starksen et al. |
| 7,588,582 B2 | 9/2009 | Starksen et al. |
| 7,618,449 B2 | 11/2009 | Tremulis et al. |
| 7,632,308 B2 | 12/2009 | Loulmet |
| 7,666,193 B2 | 2/2010 | Starksen et al. |
| 7,722,523 B2 | 5/2010 | Mortier et al. |
| 7,740,638 B2 | 6/2010 | Hyde |
| 7,753,858 B2 | 7/2010 | Starksen et al. |
| 7,766,812 B2 | 8/2010 | Schroeder et al. |
| 7,776,812 B2 | 8/2010 | Lang et al. |
| 7,832,406 B2 | 11/2010 | Ellis et al. |
| 7,850,600 B1 | 12/2010 | Piskun |
| 7,918,787 B2 | 4/2011 | Saadat |
| 8,388,680 B2 | 3/2013 | Starksen et al. |
| 8,882,713 B1 * | 11/2014 | Call ............... A61M 25/09 604/164.01 |
| 9,616,197 B2 | 4/2017 | Serina et al. |
| 2001/0005787 A1 | 6/2001 | Oz et al. |
| 2001/0014800 A1 | 8/2001 | Frazier et al. |
| 2001/0023332 A1 | 9/2001 | Hahnen |
| 2001/0031979 A1 | 10/2001 | Ricci |
| 2001/0041821 A1 | 11/2001 | Wilk |
| 2001/0047165 A1 | 11/2001 | Makower et al. |
| 2002/0007190 A1 | 1/2002 | Wulfman et al. |
| 2002/0013571 A1 | 1/2002 | Goldfarb et al. |
| 2002/0013621 A1 | 1/2002 | Stobie et al. |
| 2002/0026201 A1 | 2/2002 | Foerster et al. |
| 2002/0029080 A1 | 3/2002 | Mortier et al. |
| 2002/0035361 A1 | 3/2002 | Houser et al. |
| 2002/0035393 A1 | 3/2002 | Lashinksi et al. |
| 2002/0042621 A1 | 4/2002 | Liddicoat et al. |
| 2002/0065536 A1 | 5/2002 | Hart et al. |
| 2002/0072757 A1 | 6/2002 | Ahmed et al. |
| 2002/0077524 A1 | 6/2002 | Schweich, Jr. et al. |
| 2002/0087048 A1 | 7/2002 | Brock et al. |
| 2002/0087049 A1 | 7/2002 | Brock et al. |
| 2002/0087148 A1 | 7/2002 | Brock et al. |
| 2002/0087169 A1 | 7/2002 | Brock et al. |
| 2002/0095167 A1 | 7/2002 | Liddicoat et al. |
| 2002/0095175 A1 | 7/2002 | Brock et al. |
| 2002/0133092 A1 | 9/2002 | Oslund et al. |
| 2002/0138044 A1 | 9/2002 | Streeter et al. |
| 2002/0156526 A1 | 10/2002 | Hlavka et al. |
| 2002/0161378 A1 | 10/2002 | Downing |
| 2002/0165486 A1 | 11/2002 | Bertolero et al. |
| 2002/0173841 A1 | 11/2002 | Ortiz et al. |
| 2002/0183787 A1 | 12/2002 | Wahr et al. |
| 2002/0183835 A1 | 12/2002 | Taylor et al. |
| 2002/0193815 A1 | 12/2002 | Foerster et al. |
| 2002/0198536 A1 | 12/2002 | Trout, III et al. |
| 2003/0009196 A1 | 1/2003 | Peterson |
| 2003/0014060 A1 | 1/2003 | Wilson |
| 2003/0018358 A1 | 1/2003 | Saadat |
| 2003/0032979 A1 | 2/2003 | Mortier et al. |
| 2003/0033006 A1 | 2/2003 | Phillips et al. |
| 2003/0045893 A1 | 3/2003 | Ginn |
| 2003/0060813 A1 | 3/2003 | Loeb et al. |
| 2003/0069577 A1 * | 4/2003 | Vaska ............... A61B 18/02 606/41 |
| 2003/0069593 A1 | 4/2003 | Tremulis et al. |
| 2003/0074012 A1 | 4/2003 | Nguyen et al. |
| 2003/0078465 A1 | 4/2003 | Pai et al. |
| 2003/0078601 A1 | 4/2003 | Shikhman et al. |

(56) References Cited

U.S. PATENT DOCUMENTS

| | | |
|---|---|---|
| 2003/0078603 A1 | 4/2003 | Schaller et al. |
| 2003/0093118 A1 | 5/2003 | Ho et al. |
| 2003/0105520 A1 | 6/2003 | Alferness et al. |
| 2003/0125739 A1 | 7/2003 | Bagga et al. |
| 2003/0125767 A1 | 7/2003 | Collier et al. |
| 2003/0130731 A1 | 7/2003 | Vidlund et al. |
| 2003/0144697 A1 | 7/2003 | Mathis et al. |
| 2003/0158464 A1 | 8/2003 | Bertolero |
| 2003/0158581 A1 | 8/2003 | Levinson |
| 2003/0167062 A1 | 9/2003 | Gambale et al. |
| 2003/0167071 A1 | 9/2003 | Martin et al. |
| 2003/0171776 A1 | 9/2003 | Adams et al. |
| 2003/0199974 A1 | 10/2003 | Lee et al. |
| 2003/0220685 A1 | 11/2003 | Hlvaka et al. |
| 2003/0225420 A1 | 12/2003 | Wardle |
| 2003/0233105 A1 | 12/2003 | Gayton |
| 2003/0233142 A1 | 12/2003 | Morales et al. |
| 2003/0236535 A1 | 12/2003 | Onuki et al. |
| 2004/0003819 A1 | 1/2004 | St. Goar et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0092962 A1 | 5/2004 | Thornton et al. |
| 2004/0093024 A1 | 5/2004 | Lousararian et al. |
| 2004/0093044 A1 | 5/2004 | Rychnovsky et al. |
| 2004/0097788 A1 | 5/2004 | Mourlas et al. |
| 2004/0118415 A1 | 6/2004 | Hall et al. |
| 2004/0122450 A1 | 6/2004 | Oren et al. |
| 2004/0148020 A1 | 7/2004 | Vidlund et al. |
| 2004/0152947 A1 | 8/2004 | Schroeder et al. |
| 2004/0172046 A1 | 9/2004 | Hlavka et al. |
| 2004/0181238 A1 | 9/2004 | Zarbatany et al. |
| 2004/0186378 A1 | 9/2004 | Gesswein |
| 2004/0186486 A1 | 9/2004 | Roue et al. |
| 2004/0193191 A1 | 9/2004 | Starksen et al. |
| 2004/0204724 A1 | 10/2004 | Kissel et al. |
| 2004/0210238 A1 | 10/2004 | Nobles et al. |
| 2004/0236372 A1 | 11/2004 | Anspach, III et al. |
| 2004/0236419 A1 | 11/2004 | Milo |
| 2004/0243227 A1 | 12/2004 | Starksen et al. |
| 2005/0055052 A1 | 3/2005 | Lombardo et al. |
| 2005/0055087 A1 | 3/2005 | Starksen |
| 2005/0065550 A1 | 3/2005 | Starksen et al. |
| 2005/0075654 A1 | 4/2005 | Kelleher |
| 2005/0075723 A1 | 4/2005 | Schroeder et al. |
| 2005/0080454 A1 | 4/2005 | Drews et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0119523 A1 | 6/2005 | Starksen et al. |
| 2005/0119673 A1 | 6/2005 | Gordon et al. |
| 2005/0119735 A1 | 6/2005 | Spence et al. |
| 2005/0137689 A1 | 6/2005 | Salahieh et al. |
| 2005/0184122 A1 | 8/2005 | Hlavka et al. |
| 2005/0192629 A1 | 9/2005 | Saadat et al. |
| 2005/0197694 A1 | 9/2005 | Pai et al. |
| 2005/0209690 A1 | 9/2005 | Mathis et al. |
| 2005/0216078 A1 | 9/2005 | Starksen et al. |
| 2005/0228452 A1 | 10/2005 | Mourlas et al. |
| 2005/0251157 A1 | 11/2005 | Saadat et al. |
| 2005/0251159 A1 | 11/2005 | Ewers et al. |
| 2005/0251166 A1 | 11/2005 | Vaughan et al. |
| 2005/0251177 A1 | 11/2005 | Saadat et al. |
| 2005/0251205 A1 | 11/2005 | Ewers et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0273128 A1 | 12/2005 | Reil |
| 2005/0273138 A1 | 12/2005 | To et al. |
| 2005/0277966 A1 | 12/2005 | Ewers et al. |
| 2005/0277981 A1 | 12/2005 | Maahs et al. |
| 2005/0277983 A1 | 12/2005 | Saadat et al. |
| 2006/0025750 A1 | 2/2006 | Starksen et al. |
| 2006/0025784 A1 | 2/2006 | Starksen et al. |
| 2006/0025787 A1 | 2/2006 | Morales et al. |
| 2006/0058817 A1 | 3/2006 | Starksen et al. |
| 2006/0069429 A1 | 3/2006 | Spence et al. |
| 2006/0122633 A1 | 6/2006 | To et al. |
| 2006/0129188 A1 | 6/2006 | Starksen et al. |
| 2006/0155363 A1 | 7/2006 | LaDuca et al. |
| 2006/0161040 A1 | 7/2006 | McCarthy et al. |
| 2006/0178682 A1 | 8/2006 | Boehlke |
| 2006/0184203 A1 | 8/2006 | Martin et al. |
| 2006/0190030 A1 | 8/2006 | To et al. |
| 2006/0229697 A1 | 10/2006 | Gerdts et al. |
| 2006/0229708 A1 | 10/2006 | Powell et al. |
| 2006/0241340 A1 | 10/2006 | Schroeder et al. |
| 2006/0241656 A1 | 10/2006 | Starksen et al. |
| 2006/0264975 A1 | 11/2006 | Pipenhagen et al. |
| 2006/0270976 A1 | 11/2006 | Savage et al. |
| 2006/0271101 A1 | 11/2006 | Saadat et al. |
| 2006/0287661 A1 | 12/2006 | Bolduc et al. |
| 2007/0005081 A1 | 1/2007 | Findlay, III et al. |
| 2007/0005394 A1 | 1/2007 | Bleyendaal et al. |
| 2007/0010852 A1 | 1/2007 | Blaeser et al. |
| 2007/0010857 A1 | 1/2007 | Sugimoto et al. |
| 2007/0016250 A1 | 1/2007 | Blaeser et al. |
| 2007/0016287 A1 | 1/2007 | Cartledge et al. |
| 2007/0032820 A1 | 2/2007 | Chin-Chen et al. |
| 2007/0038293 A1 | 2/2007 | St.Goar et al. |
| 2007/0049942 A1 | 3/2007 | Hindrichs et al. |
| 2007/0051377 A1 | 3/2007 | Douk et al. |
| 2007/0055206 A1 | 3/2007 | To et al. |
| 2007/0066994 A1 | 3/2007 | Blaeser et al. |
| 2007/0093805 A1 | 4/2007 | Auth et al. |
| 2007/0100356 A1 | 5/2007 | Lucatero et al. |
| 2007/0112244 A1 | 5/2007 | McCarthy et al. |
| 2007/0112422 A1 | 5/2007 | Dehdashtian |
| 2007/0112424 A1 | 5/2007 | Spence et al. |
| 2007/0112425 A1 | 5/2007 | Schaller et al. |
| 2008/0045977 A1 | 2/2008 | To et al. |
| 2008/0045982 A1 | 2/2008 | To et al. |
| 2008/0045983 A1 | 2/2008 | To et al. |
| 2008/0051703 A1 | 2/2008 | Thornton et al. |
| 2008/0051810 A1 | 2/2008 | To et al. |
| 2008/0051832 A1 | 2/2008 | To et al. |
| 2008/0051837 A1 | 2/2008 | To et al. |
| 2008/0058765 A1 | 3/2008 | Jais et al. |
| 2008/0058868 A1 | 3/2008 | To et al. |
| 2008/0065156 A1 | 3/2008 | Hauser et al. |
| 2008/0097489 A1 | 4/2008 | Goldfarb et al. |
| 2008/0103439 A1 | 5/2008 | Torrance et al. |
| 2008/0114364 A1 | 5/2008 | Goldin et al. |
| 2008/0119882 A1 | 5/2008 | Cox |
| 2008/0172035 A1 | 7/2008 | Starksen et al. |
| 2008/0177380 A1 | 7/2008 | Starksen et al. |
| 2008/0228032 A1 | 9/2008 | Starksen et al. |
| 2008/0234701 A1 | 9/2008 | Morales et al. |
| 2008/0234702 A1 | 9/2008 | Morales et al. |
| 2008/0234704 A1 | 9/2008 | Starksen et al. |
| 2008/0234728 A1 | 9/2008 | Starksen et al. |
| 2008/0234815 A1 | 9/2008 | Starksen et al. |
| 2008/0243150 A1 | 10/2008 | Starksen et al. |
| 2008/0287828 A1 | 11/2008 | Burbank et al. |
| 2008/0294177 A1 | 11/2008 | To et al. |
| 2008/0314394 A9 | 12/2008 | Ellis et al. |
| 2009/0182417 A1 | 7/2009 | Tremulis et al. |
| 2009/0198216 A1 | 8/2009 | Muni et al. |
| 2009/0222083 A1 | 9/2009 | Nguyen et al. |
| 2009/0234318 A1 | 9/2009 | Loulmet et al. |
| 2009/0276038 A1 | 11/2009 | Tremulis et al. |
| 2010/0023056 A1 | 1/2010 | Johansson et al. |
| 2010/0049213 A1 | 2/2010 | Serina et al. |
| 2010/0076408 A1 | 3/2010 | Krever et al. |
| 2010/0076548 A1 | 3/2010 | Konno |
| 2010/0082098 A1 | 4/2010 | Starksen et al. |
| 2010/0094213 A1 | 4/2010 | Horn et al. |
| 2010/0094314 A1 | 4/2010 | Hernlund et al. |
| 2010/0121349 A1 | 5/2010 | Meier et al. |
| 2010/0185172 A1 | 7/2010 | Fabro |
| 2010/0198056 A1 | 8/2010 | Fabro et al. |
| 2010/0198192 A1 | 8/2010 | Serina et al. |

(56) References Cited

U.S. PATENT DOCUMENTS

| | | | |
|---|---|---|---|
| 2010/0198208 | A1 | 8/2010 | Napp et al. |
| 2012/0029535 | A1 | 2/2012 | Swain |
| 2012/0232565 | A1 | 9/2012 | Kveen et al. |
| 2013/0030478 | A1 | 1/2013 | Rodriguez |
| 2013/0304093 | A1 | 11/2013 | Serina et al. |
| 2014/0142619 | A1 | 5/2014 | Serina et al. |
| 2018/0043132 | A1 | 2/2018 | Serina et al. |

FOREIGN PATENT DOCUMENTS

| | | | |
|---|---|---|---|
| JP | 06-237939 | A | 8/1994 |
| JP | 9-289989 | A | 11/1997 |
| JP | 10-506812 | A | 7/1998 |
| JP | 11-318910 | A | 11/1999 |
| JP | 2000-505336 | A | 5/2000 |
| JP | 2001-500749 | A | 1/2001 |
| JP | 2003-500121 | A | 1/2003 |
| JP | 2004-500170 | A | 1/2004 |
| JP | 2004-321343 | A | 11/2004 |
| JP | 2005-021576 | A | 1/2005 |
| WO | WO 94/03227 | A1 | 2/1994 |
| WO | WO 95/15715 | A1 | 6/1995 |
| WO | WO 96/08208 | A1 | 3/1996 |
| WO | WO 96/10365 | A1 | 4/1996 |
| WO | WO 96/39942 | A1 | 12/1996 |
| WO | WO 97/27799 | A1 | 8/1997 |
| WO | WO 97/27807 | A1 | 8/1997 |
| WO | WO 97/29709 | A1 | 8/1997 |
| WO | WO 97/30638 | A1 | 8/1997 |
| WO | WO 98/07375 | A1 | 2/1998 |
| WO | WO 98/46142 | A1 | 10/1998 |
| WO | WO 99/59477 | A1 | 11/1999 |
| WO | WO 00/60995 | A2 | 10/2000 |
| WO | WO 00/67640 | A2 | 11/2000 |
| WO | WO 00/071195 | A1 | 11/2000 |
| WO | WO 01/19256 | A1 | 3/2001 |
| WO | WO 01/26586 | A1 | 4/2001 |
| WO | WO 01/37742 | A2 | 5/2001 |
| WO | WO 01/54618 | A1 | 8/2001 |
| WO | WO 02/00099 | A2 | 1/2002 |
| WO | WO 02/03892 | A1 | 1/2002 |
| WO | WO 02/051329 | A1 | 7/2002 |
| WO | WO 02/053011 | A2 | 7/2002 |
| WO | WO 02/085251 | A1 | 10/2002 |
| WO | WO 02/085252 | A1 | 10/2002 |
| WO | WO 03/088875 | A1 | 10/2003 |
| WO | WO 03/105667 | A2 | 12/2003 |
| WO | WO 03/105670 | A2 | 12/2003 |
| WO | WO 2004/037317 | A2 | 5/2004 |
| WO | WO 2004/082523 | A2 | 9/2004 |
| WO | WO 2004/082538 | A2 | 9/2004 |
| WO | WO 2005/025644 | A2 | 3/2005 |
| WO | WO 2005/062931 | A2 | 7/2005 |
| WO | WO 2005/102181 | A1 | 11/2005 |
| WO | WO 2006/037073 | A2 | 4/2006 |
| WO | WO 2006/097931 | A2 | 9/2006 |
| WO | WO 2006/116558 | A2 | 11/2006 |
| WO | WO 2007/005495 | A1 | 1/2007 |
| WO | WO 2007/021564 | A1 | 2/2007 |
| WO | WO 2007/021834 | A1 | 2/2007 |
| WO | WO 2007/035449 | A2 | 3/2007 |
| WO | WO 2007/056502 | A1 | 5/2007 |
| WO | WO 2007/100409 | A2 | 9/2007 |
| WO | WO 2008/028135 | A2 | 3/2008 |
| WO | WO 2008/042987 | A2 | 4/2008 |
| WO | WO 2008/048626 | A2 | 4/2008 |
| WO | WO-2010/085456 | A1 | 7/2010 |
| WO | WO 2010/085457 | A1 | 7/2010 |

OTHER PUBLICATIONS

Final Office Action dated Aug. 11, 2016, for U.S. Appl. No. 14/052,593, filed Oct. 11, 2013, 10 pages.

International Search Report dated Dec. 8, 2006, for PCT Patent Application No. PCT/US/2006/030260, filed on Aug. 2, 2006, 3 pages.

Non-Final Office Action dated Aug. 19, 2009, for U.S. Appl. No. 11/583,627, filed Oct. 18, 2006, 14 pages.

Non-Final Office Action dated Nov. 23, 2010, for U.S. Appl. No. 11/583,627, filed Oct. 18, 2006, 13 pages.

Non-Final Office Action dated Apr. 11, 2013, for U.S. Appl. No. 12/657,422, filed Jan. 19, 2010, 8 pages.

Notice of Allowance dated Nov. 6, 2012, for U.S. Appl. No. 11/583,627, filed Oct. 18, 2006, 7 pages.

Notice of Allowance dated Jul. 3, 2012, for U.S. Appl. No. 11/583,627, filed Oct. 18, 2006, 7 pages.

Written Opinion of the International Searching Authority dated Dec. 8, 2006, for PCT Patent Application No. PCT/US/2006/030260, filed on Aug. 2, 2006, 7 pages.

Written Opinion of the International Searching Authority dated May 6, 2008 for PCT Application PCT/US07/22122, filed on Oct. 16, 2007, 7 pages.

International Search Report and Written Opinion for PCT/US16/21065, dated May 19, 2016, 12 pages.

European Search Report dated Dec. 6, 2011, for EP Patent Application No. 11187159.6, filed on Oct. 16, 2007, 6 pages.

De Simone, R. et al. (Apr. 15, 1993). "Adjustable Tricuspid Valve Annuloplasty Assisted by Intraoperative Transesophageal Color Doppler Echocardiography," Am. J. Cardiol. 71(11):926-931.

De Simone, R. et al. (Apr. 1, 1994). "Adjustable Annuloplasty for Tricuspid Insufficiency with External Control," Reader's Comments and Reply, Am. J. Cardiol. 73(9):721-722.

Downing, S.W. et al. (2002). "Feasibility of Off-Pump ASD Closure Using Real-Time 3-D Echocardiography," The Heart Surgery Forum 5(2):96-99.

Final Office Action dated Dec. 26, 2007, for U.S. Appl. No. 10/776,682, filed Feb. 10, 2004, 6 pages.

Final Office Action dated Jan. 12, 2009, for U.S. Appl. No. 10/776,682, filed Feb. 10, 2004, 8 pages.

Final Office Action dated May 8, 2009, for U.S. Appl. No. 11/201,949, filed Aug. 10, 2005, 10 pages.

Final Office Action dated Apr. 15, 2010, for U.S. Appl. No. 11/201,949, filed on Aug. 10, 2005, 8 pages.

Final Office Action dated Oct. 22, 2010, for U.S. Appl. No. 10/776,682, filed Feb. 10, 2004, 10 pages.

Final Office Action dated Jun. 6, 2011, for U.S. Appl. No. 11/201,949, filed Aug. 10, 2005, 10 pages.

Final Office Action dated Nov. 28, 2011, for U.S. Appl. No. 11/201,949, filed Aug. 10, 2005, 8 pages.

Final Office Action dated Jan. 24, 2014, for U.S. Appl. No. 11/201,949, filed Aug. 10, 2005, 10 pages.

International Preliminary Report on Patentability dated Apr. 22, 2008, for PCT Application PCT/US2007/022122 filed on Oct. 16, 2007, 8pages.

International Search Report dated Apr. 2, 2007, for PCT Application No. PCT/US2006/043597, filed Nov. 8, 2006, 7 pages.

International Search Report dated May 6, 2008 for PCT Application PCT/US07/22122 filed on Oct. 16, 2007, 2 pages.

International Search Report and Written Opinion dated Mar. 9, 2010, for PCT Patent Application No. PCT/US/2010/021440, filed on Jan. 19, 2010, 6 pages.

International Search Report and Written Opinion dated Mar. 19, 2010, for PCT Patent Application No. PCT/US2010/021437, filed on Jan. 19, 2010, 9 pages.

Nagy, Z.L. et al. (Dec. 2000). "Mitral Annuloplasty with a Suture Technique," European Journal of Cardio-thoracic Surgery 18(6):739-740.

Non-Final Office Action dated Oct. 23, 2006, for U.S. Appl. No. 10/776,682, filed Feb. 10, 2004, 14 pages.

Non-Final Office Action dated Nov. 30, 2006, for U.S. Appl. No. 10/776,682, filed Feb. 10, 2004, 14 pages.

Non-Final Office Action dated Aug. 30, 2007, for U.S. Appl. No. 11/270,034, filed Nov. 8, 2005, 10 pages.

Non-Final Office Action dated Aug. 6, 2008, for U.S. Appl. No. 10/776,682, filed Feb. 10, 2004, 7 pages.

(56) References Cited

OTHER PUBLICATIONS

Non-Final Office Action dated Nov. 26, 2008, for U.S. Appl. No. 11/201,949, filed Aug. 10, 2005, 7 pages.
Non-Final Office Action dated Jul. 6, 2009, for U.S. Appl. No. 10/776,682, filed Feb. 10, 2004, 9 pages.
Non-Final Office Action dated Oct. 1, 2009, for U.S. Appl. No. 11/201,949, filed Aug. 10, 2005, 10 pages.
Non-Final Office Action dated Apr. 15, 2010, for U.S. Appl. No. 10/776,682, filed Feb. 10, 2004, 9 pages.
Non-Final Office Action dated Sep. 14, 2010, for U.S. Appl. No. 11/201,949, filed Aug. 10, 2005, 10 pages.
Non-Final Office Action dated Oct. 18, 2011, for U.S. Appl. No. 10/776,682, filed Feb. 10, 2004, 7 pages.
Non-Final Office Action dated Mar. 15, 2012, for U.S. Appl. No. 12/690,109, filed Jan. 19, 2010, 7 pages.
Non-Final Office Action dated Sep. 15, 2015, for U.S. Appl. No. 14/052,593, filed Oct. 11, 2013, 8 pages.
Notice of Reasons for Rejection dated Jul. 24, 2012, for Japanese Patent Application No. 2008-526078, filed on Aug. 2, 2006, 6 pages. (English Translation).
Shumway, S.J. et al. (Dec. 1988). "A 'Designer' Annuloplasty Ring for Patients with Massive Mitral Annular Dilatation," Ann. Thorac. Surg. 46(6):695-696.
Supplementary European Search Report dated Jun. 2, 2010, for EP Patent Application No. 07852809.8, filed on Oct. 16, 2007, 8 pages.
Towne, W.D. (1973). "Letter to the Editor: Classification of Chordae Tendineae," Circulation 47:209.
U.S. Appl. No. 61,160,670, filed Mar. 16, 2009, by Fabro et al.
U.S. Appl. No. 61/083,109, filed Jul. 23, 2008, by Johansson, Peter.
U.S. Appl. No. 61/104,681, filed Oct. 10, 2008, by Serina et al.
U.S. Appl. No. 61/104,686, filed Oct. 10, 2008, by To et al.
U.S. Appl. No. 61/145,964, filed Jan. 20, 2009, by Fabro, Mariel.
U.S. Appl. No. 61/160,018, filed Mar. 13, 2009, by Johansson, Peter.
U.S. Appl. No. 61/160,230, filed Mar. 13, 2009, by Meier et al.
U.S. Appl. No. 61/178,910, filed May 15, 2009, by Serina et al.
U.S. Appl. No. 61/178,938, filed May 15, 2009, by Fabro, Mariel.
Notice of Allowance dated Feb. 23, 2017, for U.S. Appl. No. 14/052,593, filed Oct. 11, 2013, 9 pages.
U.S. Appl. No. 15/474,877, filed Mar. 30, 2017, by Serina et al.

\* cited by examiner

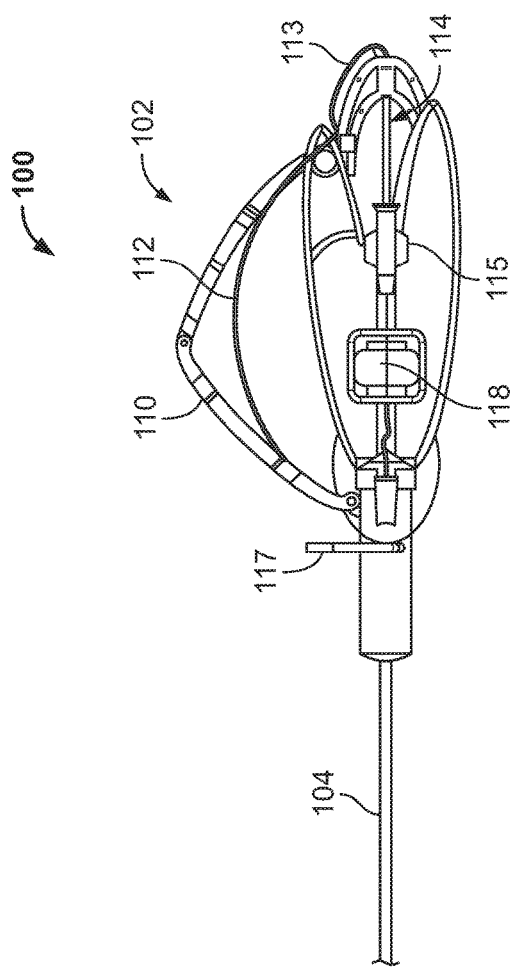
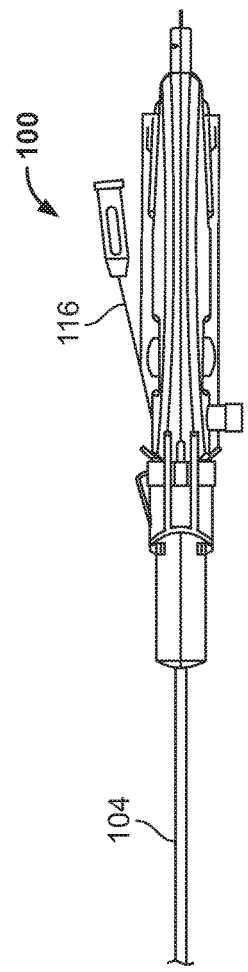
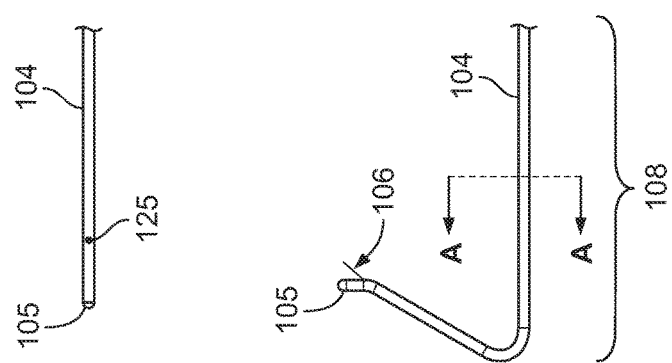
FIG. 1A
FIG. 1B

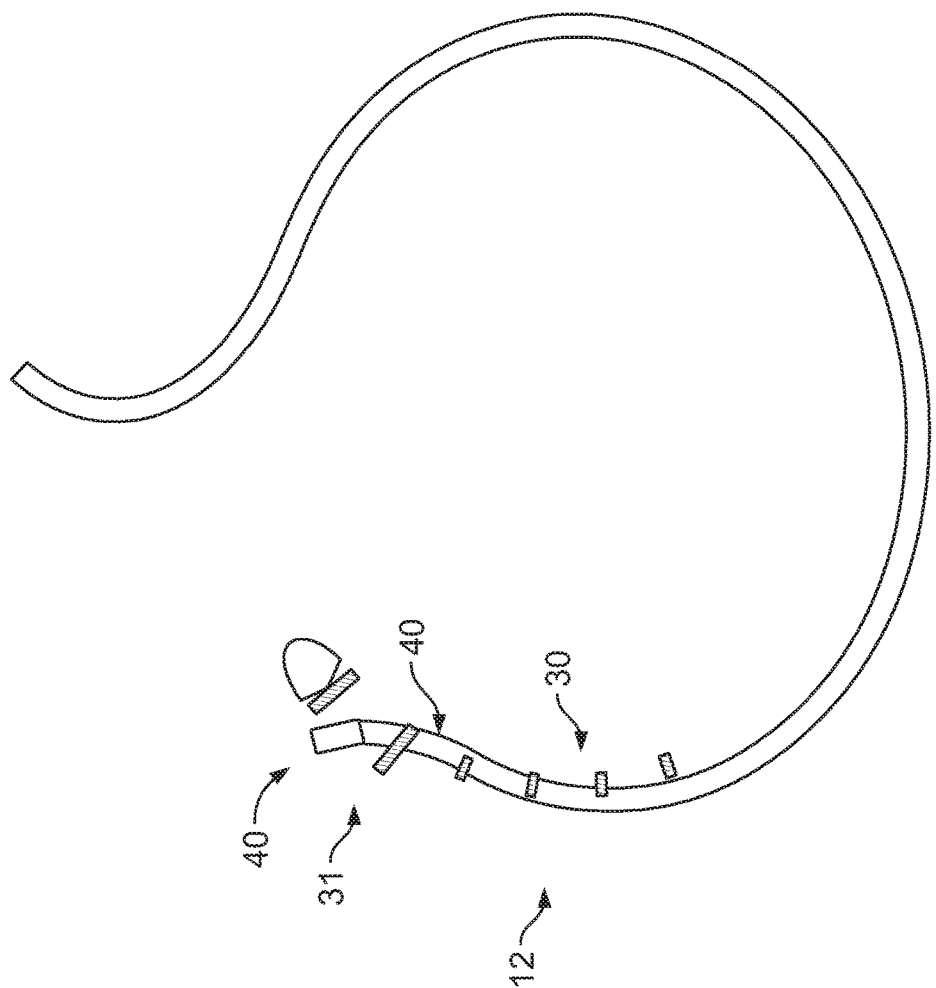

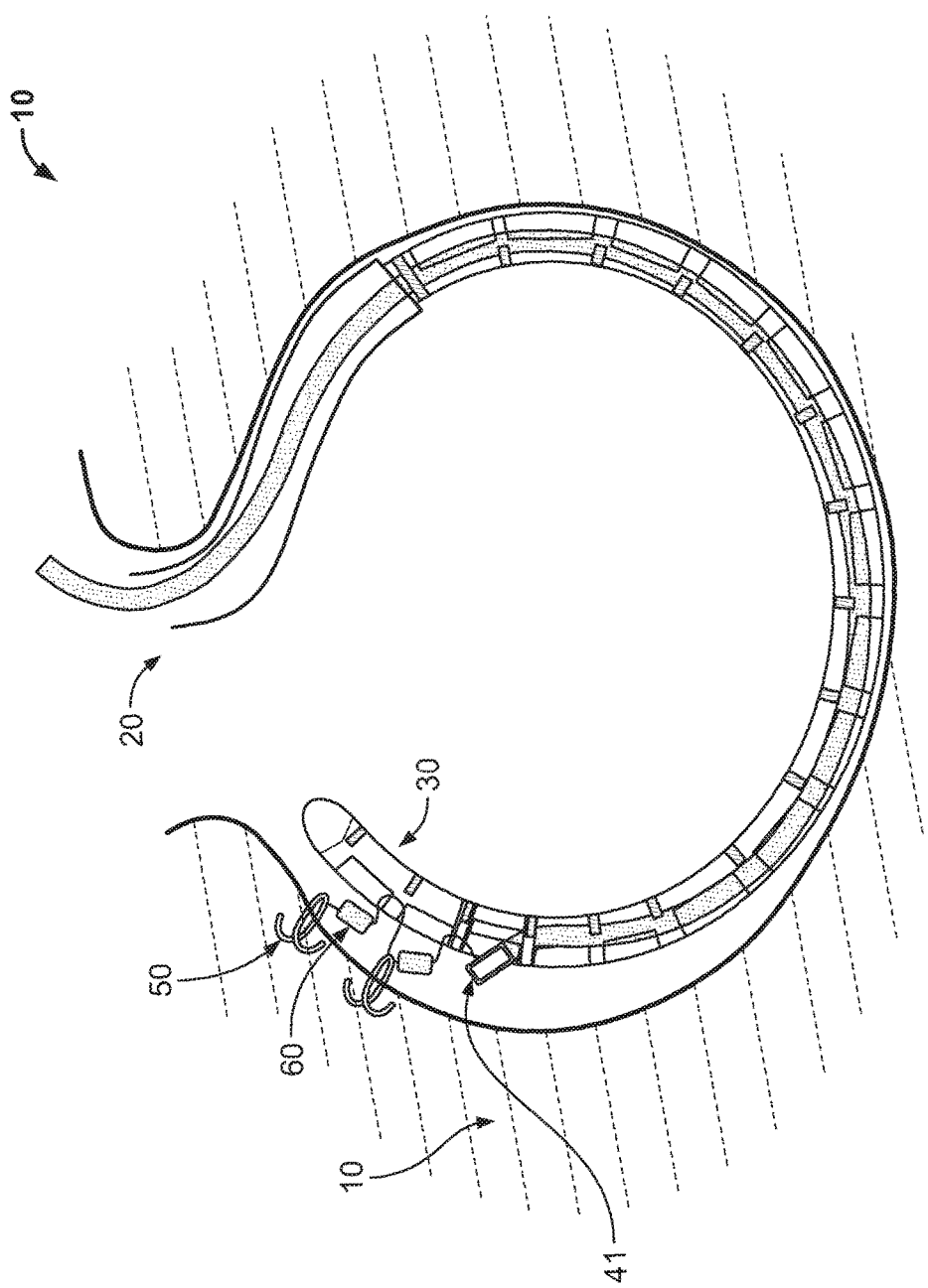

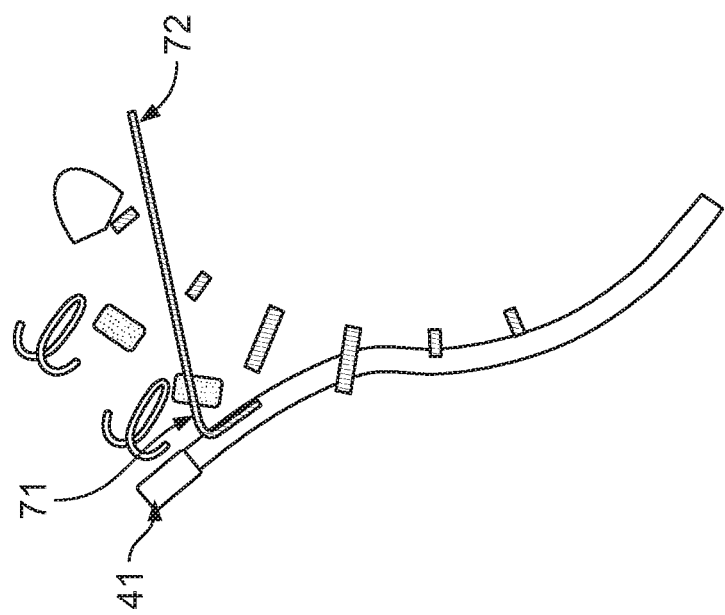

DEVICES AND METHODS OF VISUALIZING AND DETERMINING DEPTH OF PENETRATION IN CARDIAC TISSUE

CROSS-REFERENCE TO RELATED APPLICATIONS

This application claims priority to U.S. Provisional Patent Application No. 62/128,628, filed on Mar. 5, 2015, which is hereby incorporated by reference in its entirety.

BACKGROUND

Many technologies have been employed in order to visualize or locate cardiac tissue in the beating heart, including ultrasound, contrast enhanced fluoroscopy, electrical sensors, and direct visualization via a small camera or endoscope surrounded by a transparent fluid such as saline.

Each of these technologies is has its limitations, including resolution, contrast-induced nephropathy (CIN), and/or fluid overload, among others. Resolution with transesophageal echo (TEE) can be insufficient, while at the same time it is difficult to obtain an absolute orientation, given the degrees of freedom of the probe. Electrical sensors can be effective to signal contact with tissue, but are prone to error when used to determine depth of penetration below the surface of the tissue. In addition to CIN mentioned above, fluoroscopic interpretation is made more difficult by the transient nature of the contrast injection, and can be exacerbated further by the shape of the heart chamber. For example, fluoroscopic short axis views of the left ventricle can be difficult to interpret for patients with conditions such as heart failure or mitral valve regurgitation. These conditions can necessitate the use of a larger volume of contrast to obtain an adequate image. The inability to precisely assess the cardiac tissue in a beating heart renders it difficult to perform procedures with the precision needed to adequately treat these patients.

BRIEF SUMMARY

Disclosed herein are devices and methods for assessing the surface of a target cardiac tissue and for delivering a tissue anchor to cardiac tissue at a preselected depth within the endocardium. In one variation, a delivery device may comprise an elongate body, a tissue anchor disposed within a first longitudinal lumen of the elongate body, and a tissue depth indicator slidable within a second longitudinal lumen of the elongate body. The tissue depth indicator may have a first configuration where the tissue depth indicator extends tangentially toward and/or past the distal tip/end of the elongate body and a second configuration where the tissue depth indicator points or extends sharply away from the distal tip of the elongate body. In the first configuration, the tissue depth indicator may be capable of delineating the boundary and/or surface structures of the target tissue. The tissue depth indicator may transition to the second configuration when the distal tip of the elongate body has been advanced to a preselected depth into the target tissue. Optionally, some delivery catheters may further comprise a penetration depth limiter that resists or limits penetration of the delivery catheter into the tissue after a preselected depth has been reached. In some variations, a tissue depth indicator may also be configured to resist or limit the penetration of the delivery catheter into tissue.

One variation of a tissue anchor delivery device may comprise an elongate body comprising a proximal end, a distal end, a first longitudinal lumen that terminates at a first distal opening located at the distal end of the elongate body, and a second longitudinal lumen that terminates at a second distal opening located proximal to the distal end of the elongate body, a tissue anchor disposed in the first longitudinal lumen and configured to exit the first distal opening when deployed into tissue, and a tissue depth indicator. The anchor delivery catheter may comprise a push member slidably disposed within the first longitudinal lumen and configured to contact and distally advance the tissue anchor, and a stop structure located within the first longitudinal lumen and configured to restrict sliding the push tube past a selected location along the first longitudinal lumen. The tissue depth indicator may be slidable within the second longitudinal lumen such that a distal portion of the tissue depth indicator exits the second distal opening. The distal portion of the tissue depth indicator may comprise a first configuration where the distal portion extends toward the distal end of the elongate body and a second configuration where the distal portion extends away from the distal end of the elongate body, and where the tissue depth indicator is configured to transition from the first configuration to the second configuration after the distal end of the elongate body has penetrated a tissue surface at a pre-selected depth. In the first configuration, the distal portion of the indicator wire may form an obtuse angle with respect to the second longitudinal lumen, and in the second configuration, the distal portion of the indicator wire may form an acute angle with respect to the second longitudinal lumen. For example, the obtuse angle may be from about 90 degrees to about 180 degrees (e.g., about 120 degrees), and the acute angle may be from about 0 degrees to about 89 degrees (e.g., about 80 degrees). In the first configuration, sliding the tissue depth indicator within the second longitudinal lumen may vary the length of the distal portion of the indicator that exits the second longitudinal lumen. At least the distal portion of the indicator wire may be radiopaque.

A distance between the second distal opening and the distal end of the elongate body may correspond to the pre-selected penetration depth. In some variations, the tissue depth indicator may comprise a radiopaque indicator wire having a proximal portion, and the distal portion of the indicator wire may be more compliant or flexible (e.g., less stiff) than the proximal portion. For example, the proximal portion of the indicator wire may have a first stiffness and the distal portion of the indicator wire may have a second stiffness, and the second stiffness may be about 5% to about 50% of the first stiffness. The distal portion may have a length from about 1 cm to about 5 cm, e.g., about 3 cm. The distal portion of the tissue depth indicator may extend beyond the distal end of the elongate body. In some variations, the first longitudinal lumen may be distinct from the second longitudinal lumen. For example, the first longitudinal lumen and the second longitudinal lumen may be separated by a wall.

Another variation of a tissue anchor delivery device may comprise an elongate body comprising a proximal end, a distal end, a first longitudinal lumen that terminates at a first distal opening located at the distal end of the elongate body, a second longitudinal lumen that terminates at a second distal opening located proximal to the distal end of the elongate body, and a tissue depth limiter located within the second longitudinal lumen such that a distal portion of the tissue depth limiter exits the second distal opening and the distal end of the limiter is rotatably attached along an outer wall of the elongate body at a location proximal to the first distal opening, and a tissue anchor disposed in the first longitudinal lumen and configured to exit the first distal opening when deployed into tissue. The distal portion of the tissue depth limiter may comprise a first configuration where at least a length of the distal portion is substantially straight, and a second configuration wherein the distal portion has a preformed curve. Contacting the preformed curve with tissue may cause the preformed curve to rotate with respect to the elongate body and may help to prevent the distal end of the elongate body from penetrating a tissue surface beyond a pre-selected depth. The distal end of the tissue depth limiter may be radiopaque and/or may be rotatably attached along the outer wall of the elongate body at a hinge. The hinge may comprise a wire pin. In some variations, the distal end of the tissue depth limiter may comprise a loop, and the wire pin may be disposed through the loop such that in the second configuration, the tissue depth limiter rotates (e.g., with respect to the elongate body) by translating along the pin. A distance between the attachment location of the depth limiter to the elongate body and the distal end of the elongate body corresponds to the pre-selected penetration depth.

Also disclosed herein is a method of deploying a tissue anchor. One variation of a method may comprise advancing an anchor delivery device to a surface of a target tissue, where the anchor delivery device may comprise an elongate body comprising a proximal end, a distal end, a first longitudinal lumen that terminates at a first distal opening located at the distal end of the elongate body, and a second longitudinal lumen that terminates at a second distal opening located at a distance proximal to the distal end of the elongate body, a tissue anchor disposed in the first longitudinal lumen, and a tissue depth indicator located within the second longitudinal lumen. The method may further comprise sliding the tissue depth indicator within the second longitudinal lumen such that a distal portion of the tissue depth indicator exits the second distal opening to contact the surface of the target tissue, urging a distal portion of the tissue depth indicator along a length of the target tissue surface to delineate the tissue surface (e.g., the edge), advancing the distal end of the anchor delivery device into the target tissue until the distal portion of the tissue depth indicator deflects away from the tissue surface, and deploying the tissue anchor from the first distal opening into the target tissue. Urging the distal portion of the tissue depth indicator may comprise sliding the tissue depth indicator within the second longitudinal lumen. When the distal portion of the tissue depth indicator is urged along the target tissue surface, the distal portion may form an obtuse angle with respect to the second longitudinal lumen and when the distal portion of the tissue depth indicator deflects away from the tissue surface, the distal portion may form an acute angle with respect to the second longitudinal lumen. In some variations, the obtuse angle may be from about 90 degrees to about 180 degrees (e.g., about 120 degrees), and the acute angle may be from about 0 degrees to about 89 degrees (e.g., about 80 degrees). Deploying the tissue anchor may comprise advancing a push member to contact the anchor such that it exits the first distal opening. The method may further comprise advancing a tunnel catheter to the surface of the target tissue before advancing the anchor delivery device. The tunnel catheter may comprise one or more side apertures along a distal length of the tunnel catheter, and advancing the anchor delivery device may comprise advancing the anchor delivery device through a first side aperture of the tunnel catheter. In some variations, the method may further comprise withdrawing the anchor delivery device after deploying the tissue anchor and advancing a second anchor delivery device within the tunnel catheter through a second side aperture of the tunnel catheter. The target tissue may be cardiac tissue, such as ventricular tissue and/or endocardium of the left ventricle. Fluoroscopy may be used to visualize the steps of advancing the anchor delivery device, sliding the tissue depth indicator, urging the distal portion of the tissue depth indicator and deploying the tissue anchor.

Similar devices and methods may be used for the percutaneous delivery of a tissue anchor to any region of the body, including, but not limited to, blood vessels (e.g., arteries, veins), heart valves. Although the examples herein are described in the context of delivering anchors to myocardium of the left ventricle as part of a beating heart procedure, it should be understood that similar devices and methods may also be used for the delivery of anchors to myocardium of any of the heart chambers, valves, trabeculae, chordae tendineae, papillary muscles, or any cardiac structures.

BRIEF DESCRIPTION OF THE DRAWINGS

FIG. 1A depicts a side view of one variation of an anchor delivery catheter. FIG. 1B depicts a top view of the anchor delivery catheter of FIG. 1B.

FIGS. 5A-5K depict a short axis view of the left ventricle (LV), showing the aortic outflow tract and the LV chamber and the steps of a method for delivering tissue anchors using a delivery catheter comprising a depth indicator in accordance with the method depicted in FIG. 4A.

DETAILED DESCRIPTION

Figure 1C:
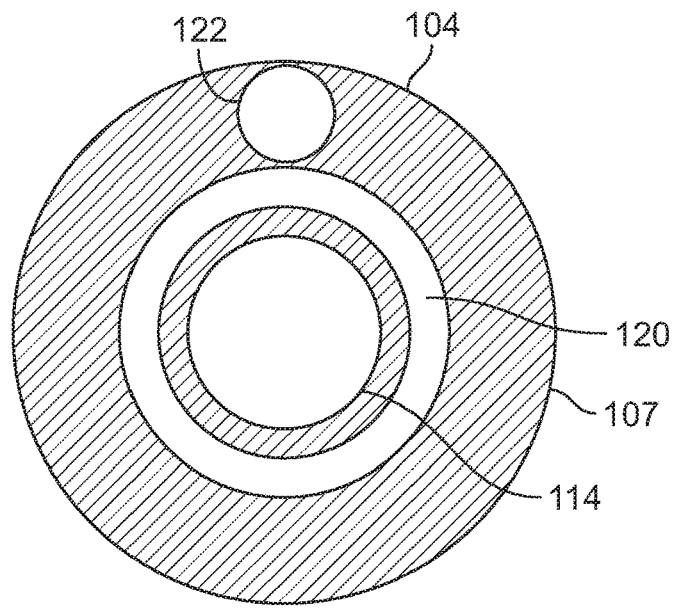
FIG. 1C depicts a cross-sectional view of one region of an anchor delivery catheter.
Figure 1D:
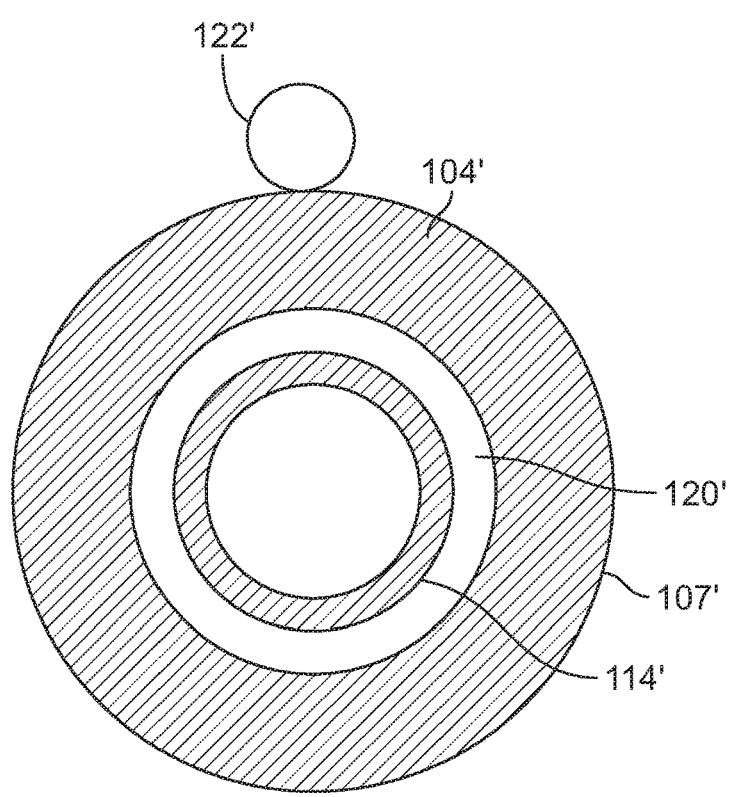
FIG. 1D depicts a cross-sectional view of another region of an anchor delivery catheter.

Disclosed herein are devices and methods for assessing the surface of a target cardiac tissue and for delivering one or more tissue anchors at a preselected depth within the cardiac tissue. Visualization of cardiac tissue is often complicated by the presence of blood and moving tissue, and as such, it can also be challenging to effectively deliver tissue anchors to a desired depth of into tissue. Penetration depth itself, without effective visualization, may be difficult to interpret, especially in diseased hearts or myocardium, which may have additional anatomical irregularities. For example, as a delivery catheter is advanced into myocardium, the actual depth achieved for a given displacement of the delivery catheter is a function of apposition between a reference starting point and the endocardium, any tissue tenting, and surface topology or trabeculations. Each of these variables can contribute significant challenges to accurately determining the actual penetration depth of the delivery catheter (and therefore, the actual delivery location of the anchor).

The devices and methods described herein allow the boundary of the cardiac surface to be visualized in a beating heart, and facilitate providing an indication as to the depth of penetration into that tissue by, for example, an anchor delivery catheter. Optionally, the devices herein below may also limit the penetration depth of a delivery catheter tip beyond a preselected depth. These features may allow a practitioner to identify the dynamic cardiac surface in real time with a degree of certainty, thereby allowing for the delivery of a tissue anchor at a preselected depth with greater precision.

One variation of an anchor delivery device may comprise an elongate body having a proximal end, a distal end, a first longitudinal lumen that terminates at a first distal opening located at the distal end and a second longitudinal lumen that terminates at a second distal opening. A tissue depth indicator may be provided within the second longitudinal lumen. The tissue depth indicator may be inserted into the second longitudinal lumen during manufacturing or may be inserted by a practitioner just prior to inserting the delivery catheter into a patient. In some variations, a tissue anchor may be disposed within the first longitudinal lumen, and may, for example, be located near a distal segment of the first longitudinal lumen. The anchor may be preloaded during manufacturing of the delivery catheter, or may be loaded by a practitioner just prior to inserting the delivery catheter into a patient. The anchor may be located just proximal to the first distal opening so that distally translating a pushing member within the first longitudinal lumen and contacting the anchor may push or advance the anchor out from the delivery catheter through the first distal opening. The tissue depth indicator may be an elongate element, such as a wire or guidewire, that has a proximal portion and a distal portion, configured to be slidably disposed within the second longitudinal lumen of the elongate body. Alternatively, in some variations, a tissue depth indicator may be disposed within the first longitudinal lumen of the elongate body (i.e., in the same longitudinal lumen as the anchor). The proximal portion may be stiffer than the distal portion, which may provide sufficient column strength so that the tissue depth indicator can be pushed from its proximal end and advanced through the second longitudinal lumen without looping or twisting. In contrast, the distal portion may be less stiff and/or more compliant than the proximal portion. For example, the distal portion of the depth indicator may be deflected, bent, angled, curved, bowed, and/or turned when it encounters a tissue surface. The compliant distal portion of the depth indicator may exit the second distal opening. The tissue depth indicator may have two configurations. In the first configuration, the distal portion may form an obtuse angle with respect to the second longitudinal lumen and/or may extend along and/or toward the distal end of the elongate body. In some variations, the distal tip of the tissue depth indicator may point towards, or in the same direction as, the distal tip of the elongate body. In the first configuration, the distal-most length of the depth indicator may extend or track along the surface of a target tissue. In the second configuration, the tissue depth indicator may form an acute angle with respect to the second longitudinal lumen and/or may deflect backward away from the distal end of the elongate body and/or the surface of the target tissue. In some variations, the distal portion of the depth indicator in the first configuration may have a relatively smooth or gradual curve (i.e., a relatively large radius of curvature), without any acute or sharp curves or angles. For example, there may not be an acute angle or sharp turn or inflection where the tissue depth indicator exits the second distal opening. In contrast, the distal portion of the depth indicator in the second configuration may comprise an inflection or discontinuity, such as a sharp curve, bend or angle, with a relatively abrupt change in curvature (i.e., a relatively small radius of curvature). For example, there may be an acute angle or sharp turn of inflection where the tissue depth indicator exits the second distal opening. This sharp bend may be readily visible by various imaging techniques, including fluoroscopy or transesophageal echocardiogram (TEE), which may provide a visual signal or indication of when the depth indicator has transitioned from the first configuration to the second configuration. The distance between the second distal opening (where the depth indicator exits the second longitudinal lumen) and the first distal opening may (where the anchor exits the first longitudinal lumen) may correspond to a preselected depth in tissue where the anchor is desired to be delivered. In some variations, the length of the distal portion of the depth indicator may be longer than the distance between the first and second distal openings, such that if desired, the tissue depth indicator may be advanced such it extends beyond the distal end of the elongate body.

A tissue depth indicator may comprise a radiopaque material. For example, at least the distal portion of a depth indicator wire may be radiopaque, while the proximal portion of the depth indicator may or may not be radiopaque. A depth indicator having at least a radiopaque distal portion may allow the conformational changes of the distal portion to be visualized using fluoroscopy techniques. Changes in the geometry or orientation of the depth indicator (e.g., changes in the curves of a depth indicator wire) as it interacts with myocardial tissue may help a practitioner to identify the location of the tissue surface with respect to the delivery catheter. For example, as the distal tip of the delivery catheter is advanced towards and into the target tissue, the tissue depth indicator may be in the first configuration. When the distal tip of the delivery catheter reaches a desired, preselected tissue depth, the tissue may press against the tissue depth indicator, thereby deflecting it away from the tissue surface and transitioning it to the second configuration. In the second configuration, the depth indicator may deflect away from the tissue at a sharp curve or discontinuity, as previously described.

A tissue depth indicator may be made of one or more materials. For example, a tissue depth indicator may comprise a wire or guidewire where the proximal portion is made of small diameter Nitinol or stainless steel, and the distal, tissue-contacting portion is made of a coil of platinum, platinum-iridium, tungsten or gold wound around a core wire of Nitinol or stainless steel. Alternatively, the proximal and distal portions of the indicator wire may be made of the same material(s), such as nickel titanium alloy, stainless steel, etc. Alternatively or additionally, a depth indicator wire may have a radiopaque core (e.g., a nickel titanium alloy core, stainless steel core, or scitanium core) and a polymeric exterior. For example, a depth indicator wire may have a proximal portion having a stainless steel core and a distal portion having a nickel titanium alloy core, with either the same or different polymeric exterior. In another example, a depth indicator wire may have a nickel titanium alloy core throughout its entire length, but the proximal portion may have a PTFE exterior while the distal portion may have a polymeric hydrophilic exterior. In some variations, the overall length of the indicator wire may be from about 120 cm to about 600 cm, e.g., from about 130 cm to about 300 cm, about 180 cm, about 195 cm, about 200 cm, about 300 cm, about 450 cm. The proximal portion may have a length from about 115 cm to about 595 cm, e.g., about 145 cm. The distal portion may have a length from about 1 cm to about 8 cm, e.g., about 2.5 cm, about 3 cm, about 3.5 cm, about 5 cm. The proximal portion may be constructed from a circular cross section wire with an area moment of inertia of $I=(\pi r^4)/4$, where r is the radius of the circular section, and a large modulus of elasticity (E), such that the stiffness is proportional to $I*E$. For example, the proximal portion may be constructed from a 300 series stainless steel wire with a radius of 0.15 mm (0.006 in) such that the stiffness is proportional to $I*E=84.7$ Nmm2 (0.03 lbf*in2). The distal, tissue-contacting portion may be relatively softer or more flexible, having, for example, a coil construction using a lower modulus material such as titanium, and stiffness only 5% to 50% as great as the proximal portion. In some variations, the distal portion may be about 5%, about 10%, about 25%, about 40%, about 50%, as stiff as the proximal portion. The diameter of the depth indicator wire may be from about 0.005 in to about 0.050 in, e.g., about 0.008 in, about 0.010 in, about 0.012 in, about 0.014 in, about 0.018 in, about 0.035 in, etc. In some variations, the distal portion of the depth indicator wire may have a preformed curve (e.g., a J curve) while in other variations, the distal portion may not have a preformed curve.

Optionally, some anchor delivery catheters may comprise a tissue depth limiter, which may help to resist or prevent advancing a delivery catheter beyond a certain tissue depth. This may be a safety feature to help ensure that the delivery catheter does not puncture or cut through the target tissue. In some variations, there may be a structure separate from the tissue depth indicator that resists or stops further advancement of the delivery catheter past a certain tissue depth while in other variations, the tissue depth indicator itself may resist advancement of the delivery catheter past a certain tissue depth. In one variation, an anchor delivery catheter may comprise an elongate body having a proximal end, a distal end, and a first longitudinal lumen that terminates at a first distal opening located at the distal end and a second longitudinal lumen that terminates at a second distal opening located proximal to the distal end. The tissue delivery catheter may further comprise a tissue depth limiter disposed within the second longitudinal lumen. The tissue depth limiter may have a protrusion, such as a shoulder or curved surface, that may abut against tissue and resist distal travel of the delivery catheter into tissue. The curvature of the protrusion, especially the tissue-contacting surfaces of the protrusion, may be selected such that the protrusion does not cause tissue trauma (e.g., may be an atraumatic tissue-contacting surface). In some variations, a tissue anchor may be disposed within the first longitudinal lumen, and may, for example, be located near a distal segment of the first longitudinal lumen. The anchor may be preloaded during manufacturing of the delivery catheter, or may be loaded by a practitioner just prior to inserting the delivery catheter into a patient. The anchor may be located just proximal to the first distal opening so that distally translating a pushing member and contacting the anchor may push or advance the anchor out from the delivery catheter through the first distal opening.

In one variation, a tissue depth limiter may comprise a first, low-profile configuration and a second, expanded configuration. One variation of a tissue depth limiter may comprise an elongate member, such as a wire (e.g., a flat wire), disposed within the second longitudinal lumen of the elongate body, where a distal portion of the elongate member exits the second distal opening and the distal tip of the elongate member is attached along an outer surface of the elongate body. The attachment location of the depth limiter may be at a preselected distance proximal to the distal end of the elongate body. In some variations, the preselected distance may correspond to the maximum tissue depth at which the anchor delivery catheter tip may be advanced. The distal-most end of a depth limiter may be rotatably attached to the elongate body. For example, the distal-most end of a depth limiter may be coupled to an attachment member that is attached to the elongate body such that there is a rotational degree of freedom between the distal-most end of the depth limiter and the attachment member. For example, the depth limiter may be movably coupled to the attachment member such that movement along the attachment member would cause the depth limiter to rotate around the elongate body. Alternatively or additionally, the distal-most end of the depth limiter and the attachment member may be coupled as a ball-and-socket arrangement, which may allow the depth limiter to pivot around the attachment member. In the first configuration, the depth limiter may be flush against the outer surface of the elongate body. This may be a desired configuration for navigating the anchor delivery catheter through the vasculature (and/or within the lumen of an outer catheter) before it reaches the mydocardium. Before the delivery catheter contacts the surface of the myocardium, the depth limiter may be transitioned to the second expanded configuration. The depth limiter may be expanded into the second configuration by distally advancing the depth limiter within the second longitudinal lumen. The distally-directed pushing force on the depth limiter wire may cause the distal portion of the wire to curve or rotate away from the outer surface of the elongate body, thereby having a profile and stiffness that may act as a shoulder or protrusion to abut against tissue. In some variations, the distal portion of the depth limiter wire may have a preformed or preshaped curve such that when the depth limiter wire is pushed distally, the distal portion is biased toward having the preformed or preshaped curve. For example, at least the distal portion of the depth limiter wire may be made of a shape memory and/or elastic material such that the natural or low-energy state is the expanded or curved shape, and withdrawing the depth limiter wire within a lumen constrains the wire in a straightened, high-energy state. Once the distal portion of depth limiter wire is advanced distally through the second longitudinal lumen and the second distal aperture, the depth limiter wire automatically transitions to the second, expanded configuration. At least a portion of the depth limiter in the expanded configuration is substantially perpendicular to the longitudinal axis of the delivery catheter and/or the surface of the target tissue. In some variations, a shoulder of the depth limiter extends away from the longitudinal axis of the delivery catheter. Once the distal end or tip of the delivery catheter has attained a certain tissue depth, the depth limiter contacts the tissue surface (e.g., at the shoulder of the limiter) and resists further advancement of the delivery catheter into the tissue. When the practitioner experiences this tactile indication (e.g., resistance against further advancement or distal movement), the practitioner may confirm the location of the anchor delivery catheter and/or penetration depth, and proceed to deliver the anchor from the distal end of the elongate body. After the anchor has been delivered, the depth limiter may be transitioned to the first, collapsed, configuration before the delivery catheter is withdrawn.

The distal-most end of a tissue depth limiter may be rotatably or pivotably attached to the elongate body (e.g., along the outer surface of the elongate body). In some variations, the distal portion of a tissue depth limiter may be more flexible than a proximal portion of the limiter to facilitate rotational or pivotal motion with respect to the elongate body. This may allow the depth limiter to rotate, pivot, or twist when it is in the expanded configuration. The degree and/or orientation direction of the rotation may depend on, for example, the amount of force exerted on the limiter by the tissue as the practitioner advances the delivery catheter into the tissue. That is, the deeper the penetration, the more the depth limiter may rotate. The depth limiter may rotate anywhere from about 1 degree to about 180 degrees, e.g., about 45 degrees, about 90 degrees, etc. In some variations, the rotation of the depth limiter may provide a visual signal (in addition or alternatively to a tactile signal) that a preselected depth into tissue has been attained. For example, when viewing a left ventricle from a short axis view, rotation of the depth limiter by about 90 degrees may provide a distinct visual cue (e.g., the limiter sweeping out to have a larger cross-sectional area or sweeping inward to have a smaller cross-sectional area) that the delivery catheter tip is at the preselected depth and/or that the depth limiter is pressed against the tissue surface. In variations where the tissue depth limiter comprises a radiopaque material, the conformational, rotational and/or orientation changes of the limiter can be visualized using fluoroscopy and/or transesophageal echocardiogram techniques. Alternatively, the distal-most end of a tissue depth limiter may be fixedly attached along the length of the elongate body. For example, the distal-most end may be attached to the elongate body by welding, soldering, and the like, and/or one or more adhesives.

The distal-most end of the limiter may be attached to the elongate body by any suitable rotational mechanisms, including, but not limited to, hinges, pivots, ball-and-socket joints, ball bearings, and the like. In one variation, the distal-most end of the depth limiter may comprise a loop and the rotatable attachment mechanism may comprise a curved wireform shaft or pin attached along the outer surface of the elongate body. The curved wireform shaft or pin may be in the form of a ring, or a partial ring (e.g., a U-shaped curve where the two ends are attached to the elongate body). The ring and the loop may mutually engage, thereby allowing the depth limiter to rotatably slide along the curve of the ring. In this variation, the depth limiter may sweep about 90 degrees counterclockwise with respect to a vertical axis perpendicular to the longitudinal axis of the elongate body and/or about 90 degrees clockwise with response to the vertical axis, depending on the direction and magnitude of force applied on the depth limiter by the surface of the target tissue. The distance of the attachment mechanism from the distal end of the elongate body may correspond to a preselected tissue penetration depth. For example, if it is desired that the tip of the anchor delivery catheter is not to be advanced past a tissue depth of about 6 mm, then the attachment mechanism may be located at about 6 mm away from the distal end of the elongate body.

The tissue depth limiter may be made of any of the materials described above for the tissue depth indicator. The stiffness of the tissue depth limiter constructed from a Nitinol flat wire of width of about 0.006 in and thickness of about 0.011 inches may be about 0.04 lbf*in$^2$ (275 Nmm$^2$). In some variations, the tissue depth limiter may comprise a flattened nickel titanium alloy wire, while in other variations, the tissue depth limiter may comprise a hypodermic tube. A depth limiter comprising a flattened wire may have a width from about 0.010 in to about 0.04 in, e.g., about 0.015 in, about 0.025 in, about 0.0.030 in, about 0.035 in, etc., and a thickness from about 0.005 in to about 0.015 in. The second longitudinal lumen of the elongate body within which the depth limiter is disposed may have a width of about 0.0.018 in to about 0.043 in, e.g., about 0.02 in, about 0.025 in, about 0.04 in, etc. When the depth limiter is in the first collapsed configuration, the overall height of a distal section of the anchor delivery catheter (i.e., the sum of the diameter of the elongate body and the second longitudinal lumen) may be from about 0.06 in to about 0.10 in for example, about 0.09 in to about 0.11 in, e.g., about 0.098 in, about 0.1 in, etc. In the second expanded configuration, the overall height of the distal section of the anchor delivery catheter (i.e., the sum of the diameter of the elongate body and the height of the expanded depth limiter) may be from about 0.15 in to about 0.35 in for example, about 0.2 in to about 0.5 in, e.g., about 0.283 in, about 0.3 in, about 0.38 in, about 0.45 in, etc.

Any of the anchor delivery catheters comprising a tissue depth indicator and/or a tissue depth limiter described herein may further comprise a push member, such as a push tube, within the first longitudinal lumen of the elongate body to deploy an anchor disposed within that lumen. The elongate body may optionally have one or more curves, where the one or more curves define one or more distinct planes that may be located at one or more angles with respect to each other. Alternatively or additionally, the elongate body of the anchor delivery catheter may be steerable. The actuation of the push member, along with the control of the tissue depth indicator and/or tissue depth limiter, and/or any steering mechanisms of the delivery catheter, may be controlled at a proximal handle of the delivery catheter. In some variations, one or more tethers or sutures may be threaded through the anchor to be delivered (e.g., where the implanted device comprises a series of tethered anchors), and the proximal end of the one or more tethers or sutures may be coupled to the proximal handle of the delivery catheter. For example, the proximal handle may comprise a suture holder that is configured to releasably retain a suture, a push tube actuator, and a tissue depth indicator port. Optionally, the proximal handle may comprise a tissue depth limiter port. A practitioner may control the length of the depth limiter or indicator that exits the distal opening of the second longitudinal lumen by advancing or retracting/withdrawing the proximal portion of the limiter and/or indicator at these proximal ports. Optionally, the location of the depth indicator and/or limiter may be locked at a proximal portion. In some cases, a tissue depth indicator wire may be withdrawn entirely from the delivery catheter. The push tube actuator may comprise a locking mechanism so that the position of the push tube may be secured once it has been advanced to the desired location. Any portion of these components may be radiopaque, as may be desirable for fluoroscopic monitoring of the progress of the procedure. For example, the distal tip of the elongate body and/or a distal length of the tissue depth indicator and/or limiter may be radiopaque.

Any of the anchor delivery catheters described herein may also comprise a push tube stop structure within the first longitudinal lumen of the elongate body. The push tube stop structure may prevent the push tube from being over-advanced, e.g., advanced out of the elongate body. In some variations, an anchor delivery catheter may be one catheter in a system of catheters used in a multi-step intravascular procedure. In these procedures, an anchor delivery catheter may be advanced within the lumen of one or more other catheters, and some anchor delivery catheters may comprise features to limit relative motion between nested catheter elements, as well as to help direct orientation of the anchor delivery catheter with respect to outer catheter elements. For example, an anchor delivery catheter may optionally comprise stop elements that limit its travel within a guide catheter and/or a multi-window catheter so that the length of the delivery catheter that extends out from these catheters is restricted. These stop elements may be external to the anchor delivery catheter, but internal to the outer guide catheter and/or multi-window guide catheter (e.g., the stop elements do not contact the target tissue). In some variations, a stop element may be a flat ribbon, wire loop, spring, protrusion, wing or petal. Additional details regarding anchor delivery catheters with stop elements that limit its travel within a guide catheter and/or multi-window catheter without contacting tissue are provided in co-pending U.S. Pat. Appln. Pub. No. 2014/0142619, filed Oct. 11, 2013, which is hereby incorporated by reference in its entirety.

Figure 1E:
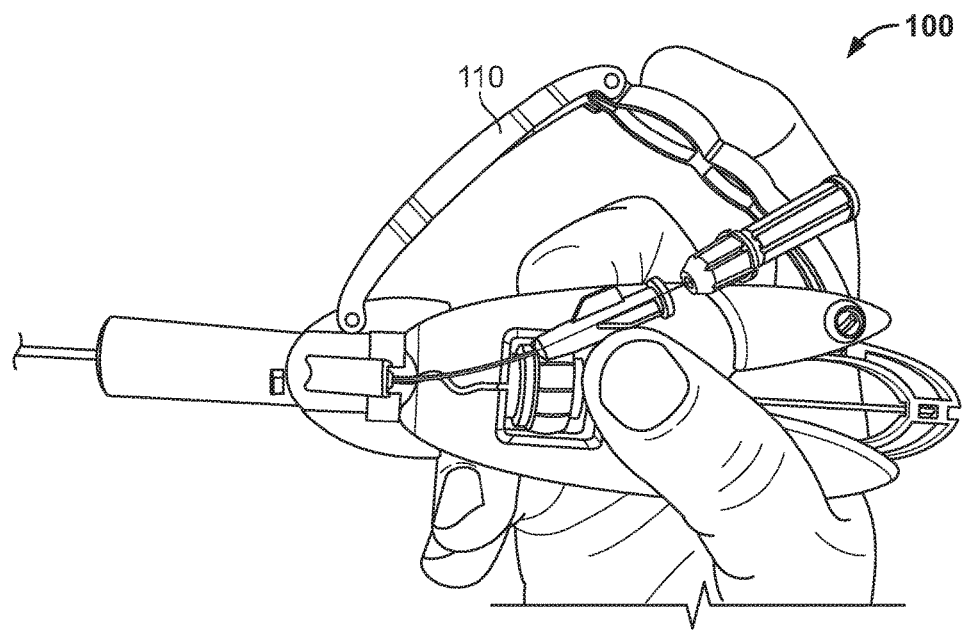
FIGS. 1E and 1F depict the operation of a proximal portion of the anchor delivery catheter of FIG. 1A.
Figure 1F:
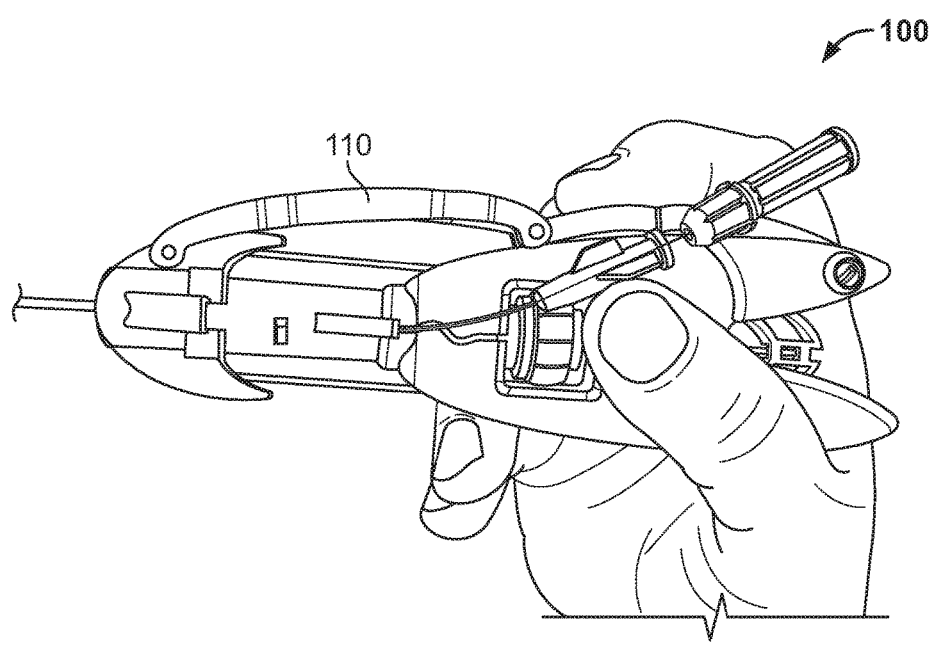

One variation of an anchor delivery catheter comprising a tissue depth indicator is depicted in FIGS. 1A-1F. Anchor delivery catheter 100 may comprise a proximal handle 102, an elongate body 104, and a tissue depth indicator 106. The distal section 108 of the elongate body 104 may comprise one or more curves. The proximal handle 102 may comprise a deployment handle 110, a separable suture holder 112 configured to retain a suture 113, a push tube 114, a safety retainer clip 117, and a tissue depth indicator port 116. The proximal handle 102 may also comprise a touhy borst valve 118 with a flush port. One variation of a cross-sectional view of the distal section 108 of the elongate body 104 is depicted in FIG. 1C. As depicted there, the elongate body 104 comprises a first longitudinal lumen 120 and a second longitudinal lumen 122. The first longitudinal lumen 120 may extend from the proximal handle (e.g., in communication with a port 115 through which the push tube 114 is inserted) and terminate at a distal opening 105. The second longitudinal lumen may extend from the proximal handle (e.g., in communication with depth indicator port 116) and terminate at a second distal opening 125 (FIG. 1A). The push tube 114 is disposed within the first longitudinal lumen 120 and is configured to contact an anchor (not shown) in order to deploy it from a distal opening 105 of the elongate body 104. The push tube 114 may be coupled to the deployment handle 110 such that manual actuation of the handle 110 distally translates the push tube 114 to deploy the anchor, as depicted in FIGS. 1E and 1F. FIG. 1E depicts the deployment handle 110 prior to anchor deployment (e.g., the anchor-stowed configuration). FIG. 1F depicts the deployment handle 110 as it is depressed by a practitioner to deploy the anchor (e.g., the anchor-deployed configuration). Although the variation in FIG. 1C has a second longitudinal lumen 112 that is located within the boundaries of an outer wall 107 of the elongate body 104, the second longitudinal lumen may be located outside of the outer wall of the elongate body. For example, the variation depicted in FIG. 1D has a second longitudinal lumen 122' that is located external to the outer wall 107' of the elongate body 104'. In some variations, the arrangement of the first and second longitudinal lumens depicted in FIG. 1D may be used at a distal-most section of the elongate body (e.g., the section of the elongate body that may contact and/or penetrate tissue) while the arrangement of the first and second longitudinal lumens depicted in FIG. 1C may be used at a more proximal section of the elongate body.

FIGS. 2A-2H depict one variation of an anchor delivery catheter comprising a tissue depth indicator. Anchor delivery catheter 200 comprises an elongate body 204 having a first longitudinal lumen 206 that terminates at a distal opening 208. An anchor 207 may be disposed within the first longitudinal lumen 206 such that it exits the distal opening 208 when deployed. A push tube 210 may located proximal to the anchor 207 and may be distally advanced to contact and deploy the anchor. Optionally, a push tube stop member 211 may be disposed within the first longitudinal lumen 206 to limit the distal travel of the push tube 210. For example, the push tube 210 may comprise a radiopaque marker band (not shown) that circumscribes the tube. The outer diameter of the marker may be larger than the inner diameter of stop member 211 such that when the push tube has been advanced to a selected distal location, the marker band abuts the stop member 211. In some variations, the marker band may be located about 13 mm proximally from the distal end of the push tube 210. The elongate body 204 may optionally comprise a side slot 212 in communication with the first longitudinal lumen 206 and distal opening 208. The anchor 207 may comprise a loop or eyelet 213 through which a tether or suture may be disposed. For example, the anchor may be one of a plurality of tethered anchors in a tethered anchor assembly, and tensioning the tether across the anchors may cause the length of the tissue to which these anchors are attached to shorten. The anchor 207 may be oriented within the first longitudinal lumen 206 such that the anchor loop 213 is aligned with the opening of the slot 212, which may help to facilitate threading of a tether (not shown) therethrough. The elongate body 204 may also comprise a second longitudinal lumen 214, which may extend from the proximal handle and terminate at a second distal opening 216. In some variations, the edge of the distal opening 216 may be beveled at an angle. A beveled angle at any lumen opening may help to provide an atraumatic leading edge to the second longitudinal lumen. A tissue depth indicator 230 may be disposed within the second longitudinal lumen 214 and a distal portion of the depth indicator may exit the second distal opening 216. As described previously, the length of the depth indicator that exits and/or extends from the second distal opening may be varied by advancing or retracting the depth indicator at the proximal handle. In some variations, the second longitudinal lumen 214 may have a diameter from about 0.012 in to about 0.02 in, e.g., about 0.018 in, which may be selected based on the diameter of the tissue depth indicator. The location of the second distal opening 216 may be determined at least in part by the desired penetration depth of the delivery catheter tip (i.e., the desired anchor deployment depth into tissue). In some variations, the distance D1 between the first distal opening 208 and second distal opening 216 may correspond to the desired penetration depth and/or anchor delivery depth. The desired penetration depth and/or anchor delivery depth may vary according to a number of factors, include the targeted tissue region, the anchor depth required to withstand pull-out forces to which the anchor may be subjected during/after implantation, toughness of the tissue, thickness of the tissue, etc. For example, the desired penetration and/or anchor delivery depth may be from about 1 mm to about 15 mm, e.g., about 3 mm, about 4 mm, about 5.5 mm, about 6 mm, about 8 mm, about 10 mm, about 12.5 mm, etc. Accordingly, distance D1 may vary from about 1 mm to about 15 mm, e.g., about 3 mm, about 4 mm, about 5.5 mm, about 6 mm, about 8 mm, about 10 mm, about 12.5 mm, etc.

Figure 2A:
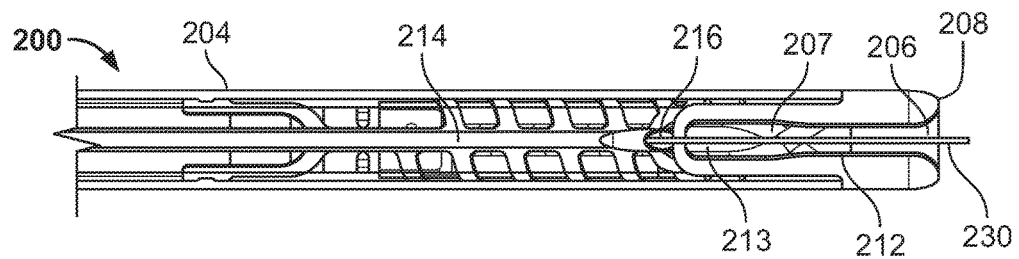
FIG. 2A is a top view of a distal portion of one variation of an anchor delivery catheter comprising a tissue depth indicator.
Figure 2B:
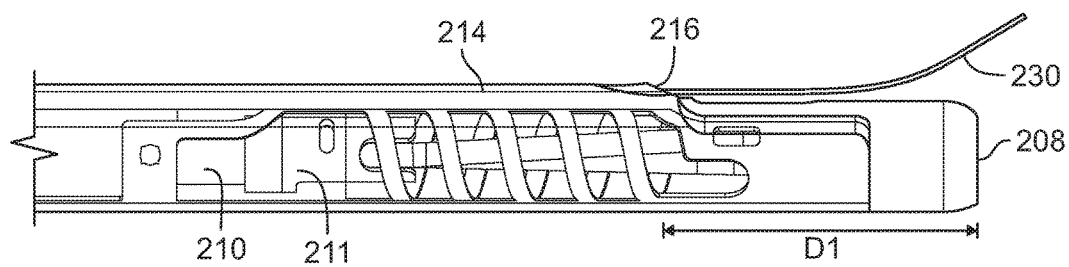
FIG. 2B is a side view of the distal portion of the anchor delivery catheter of FIG. 2A.
Figure 2C:
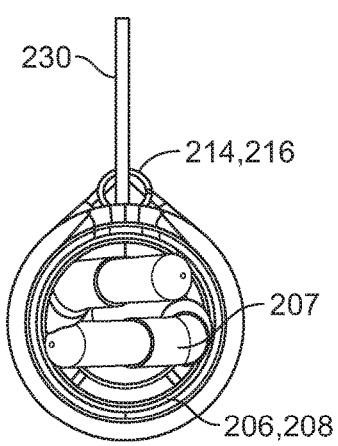
FIG. 2C is an end view of the anchor delivery catheter of FIG. 2A.
Figure 2D:
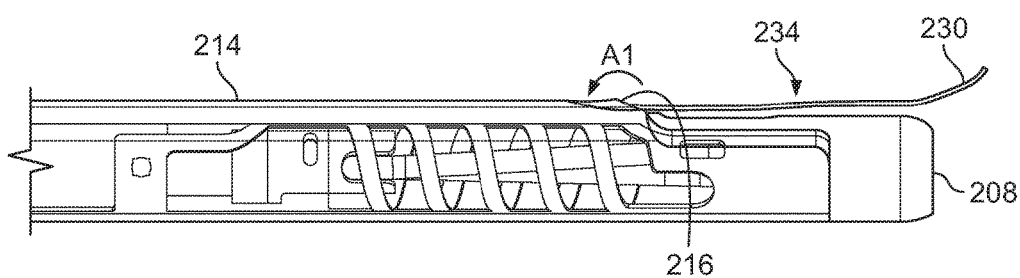
FIG. 2D depicts the anchor delivery catheter of FIGS. 2A-2C with the depth indicator in a first configuration.
Figure 2E:
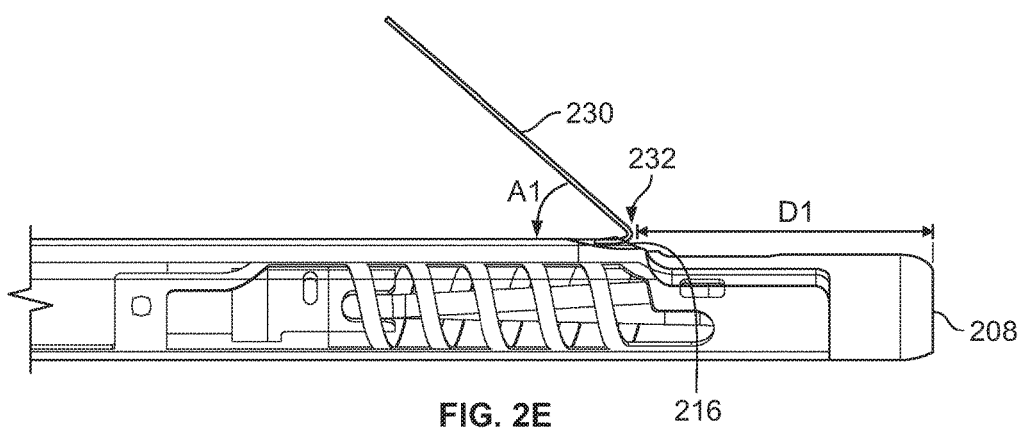
FIG. 2E depicts the anchor delivery catheter of FIGS. 2A-2C with the depth indicator in a second configuration.
Figure 2F:
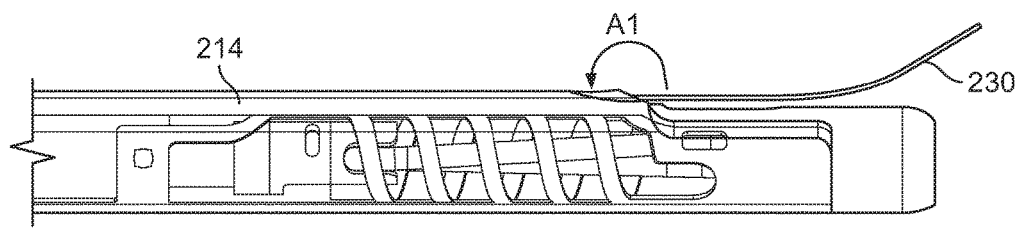
FIGS. 2F-2H depicts angular variations of the depth indicator in the first configuration.
Figure 2G:
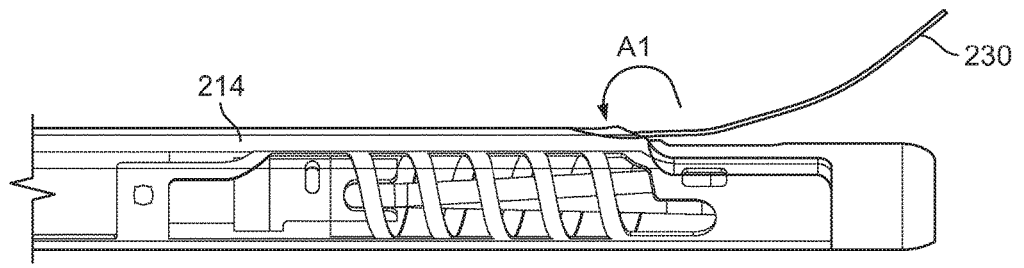
Figure 2H:
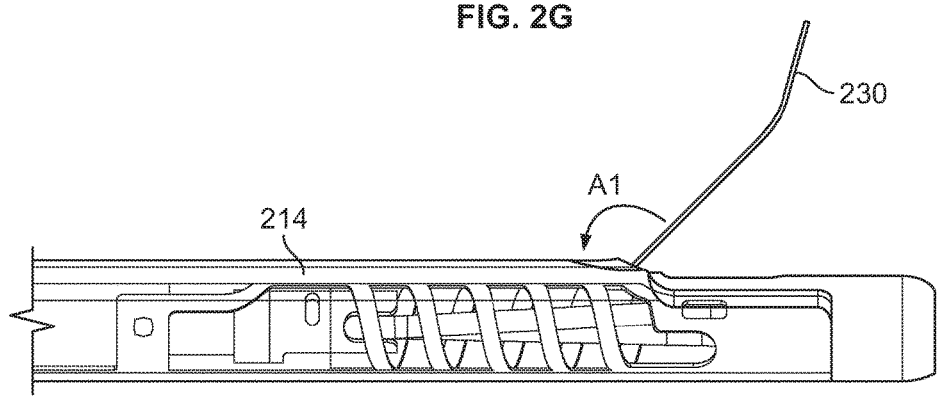

FIGS. 2D and 2E depict one variation of a tissue depth indicator 230 having a distal portion 234 that is more compliant (e.g., softer, less stiff) than a proximal portion (view blocked by the wall of the second longitudinal lumen) of the indicator. The tissue depth indicator 230 may comprise an indicator wire with a distal portion 234 that is more compliant than its proximal portion. The indicator wire 230 may have a first configuration (FIG. 2D) and a second configuration (FIG. 2E). The angle A1 between the indicator wire 230 and the second longitudinal lumen 214 may vary between the two configurations. The vertex 232 of the angle A1 may be co-localized with the second distal opening 216 (e.g., the location where the indicator wire exits the second distal opening). In the first configuration, the angle A1 may be obtuse, and in the second configuration, the angle A1 may be acute. For example, the angle A1 in the first configuration may be from about 120 degrees to about 180 degrees (see FIGS. 2D, 2F-2H), while the angle A1 in the second configuration may be from about 80 degrees to about 120 degrees (see FIG. 2E). More generally, the curvature of the indicator wire in the second configuration has a discontinuity or inflection at the point of exit that is not present in the first configuration. The indicator wire 230 may be in the first configuration when the distal tip (i.e., the distal opening 208) of anchor delivery catheter is not located at the desired tissue depth. In this first configuration, the distal portion 234 of the indicator wire 230 may extend past the distal end of the elongate body, may contact a length of the distal section of the elongate body, and/or may generally have smoother curves (i.e., the radius of the curvature does not change abruptly). The flexibility of the distal portion 234 allows the indicator wire to interrogate, track along, delineate, or otherwise be urged along the surface of the target tissue without puncturing or abrading the tissue. The curvature of a distal portion that comprises a radiopaque material may be visualized using fluoroscopic techniques, and may allow a practitioner to identify the boundary of the tissue surface, along with the topology of the tissue surface. For example, curvature of the distal portion along the surface of the tissue may also delineate any irregularities, protrusions, trabeculae, etc. on the surface of the myocardium. Advancing the distal portion 234 of the indicator wire 230 ahead of the delivery catheter may facilitate the navigation of the delivery catheter towards the tissue surface. It may also help facilitate the proper orientation of the delivery catheter with respect to the tissue surface. For example, the delivery catheter may be navigated so that the direction of its travel is substantially oriented at an angle of 20 to 80 degrees, e.g., about 30 degrees to about 45 degrees with respect to the surface of the target tissue as delineated by the distal portion of the indicator wire. As the delivery catheter is advanced into the target tissue (e.g., endocardium of a left ventricle), the tip of the delivery catheter may penetrate more deeply into the tissue, and when the penetration depth is approximately the same as the distance D1, the tissue surface may press against the compliant distal portion of the indicator, thereby causing it to deflect away from the tissue surface and/or the distal tip of the elongate body (i.e., the depth indicator transitions from the first configuration to the second configuration). Since this deflection results in an acute change or discontinuity in the curvature of the distal portion, it is readily visualized using fluoroscopic techniques. This conformational change provides a visual indication to the practitioner that the distal tip of the delivery catheter has penetrated the tissue at a depth that is approximately the same as the distance D1. The anchor may then be deployed from the delivery catheter.

Figure 3A:
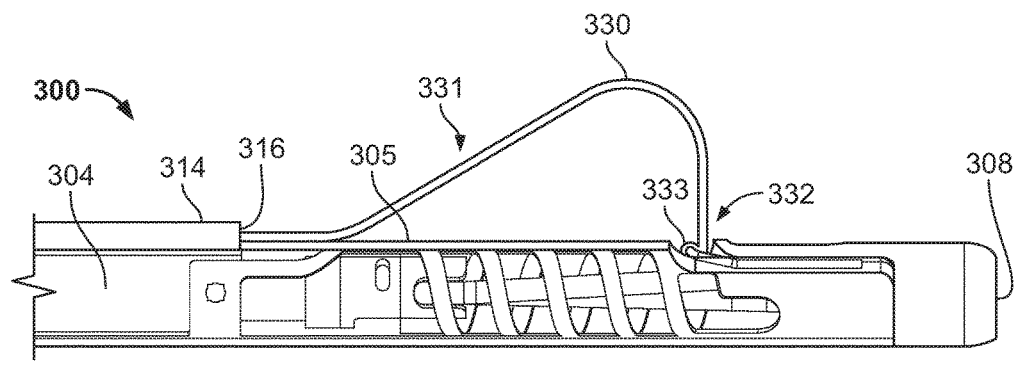
FIG. 3A is a side view of a distal portion of another variation of an anchor delivery catheter comprising a tissue depth limiter in an expanded configuration.
Figure 3B:
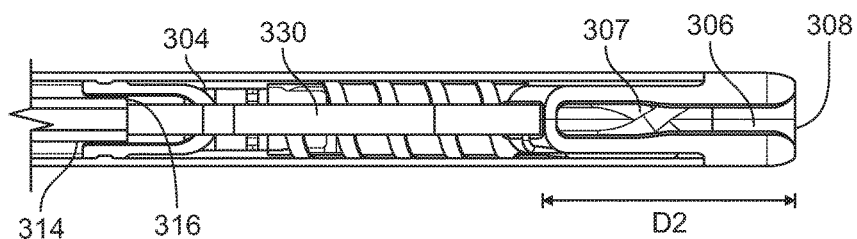
FIG. 3B is a top view of the distal portion of the anchor delivery catheter of FIG. 3A.
Figure 3C:
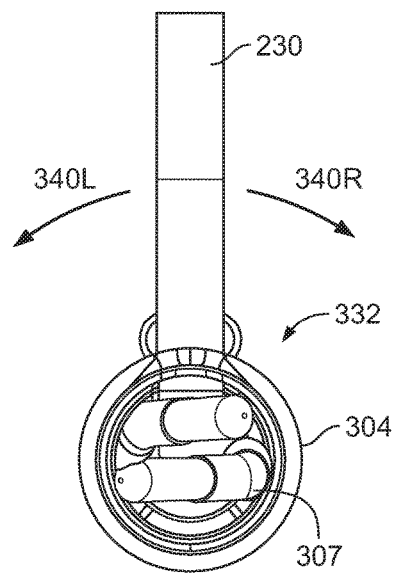
FIG. 3C is an end view of the anchor delivery catheter of FIG. 3A.

Some variations of an anchor delivery catheter may alternatively or additionally comprise a tissue depth limiter, which may resist penetration of the distal tip of the delivery catheter past a preselected depth. This may provide a tactile signal to a practitioner that a desired (or maximum) penetration depth has been attained. FIGS. 3A-3D depict one variation of an anchor delivery catheter 300 comprising an elongate body 304 and a tissue depth limiter 330. The elongate body 304 may have a first longitudinal lumen 306 that extends from the proximal handle and terminates at a first distal opening 308 and a second longitudinal lumen 314 that extends from the proximal handle and terminates at a second distal opening 316. A tissue depth limiter 330 may be disposed within the second longitudinal lumen 314 and a distal portion 331 of the depth limiter 330 may exit the second distal opening 316. The distal end 333 of the depth limiter 330 may be attached to the elongate body 304. The distance D2 between the attachment location of the depth limiter 330 and the distal tip/opening of the elongate body may correspond to the desired or maximum tissue penetration depth. Distance D1 may be, for example, from about 1 mm to about 15 mm, e.g., about 3 mm, about 4 mm, about 5.5 mm, about 6 mm, about 8 mm, about 10 mm, about 12.5 mm, etc. In some variations, the distal portion 331 of the depth limiter may comprise a preformed curve, while in other variations, the distal portion does not have a preformed curve. The depth limiter 330 may have a first collapsed configuration (FIG. 3E) and a second expanded configuration (FIG. 3A). In the first configuration, the depth limiter may be retracted proximally such that the distal portion is substantially flush with (e.g., extends along) the outer surface 305 of the elongate body 304. In the second configuration, the depth limiter may be advanced distally such that a longer length of the distal portion exits the second distal opening and allows for the distal portion to form a curve or loop, as shown in FIG. 3A. In some variations, the distal portion 331 may have a preformed curve that automatically expands when a sufficient length of the depth limiter has exited the second longitudinal lumen. For example, the depth limiter 330 may comprise a shape-memory material that is preformed with a distal curve. In the first configuration, the depth limiter is compressed to a straightened form within the second longitudinal lumen. In the second configuration, the distal portion with the preformed curve automatically assumes its expanded shape when it exits the second distal opening and is released from the second longitudinal lumen. The shape of the atraumatic curve may be selected such that a larger surface of the curve is located generally perpendicularly to the longitudinal axis of the elongate body. This may help to provide sufficient resistance to forward-travel of the delivery catheter when the desired or maximum penetration depth is attained, but also help to provide an atraumatic tissue-contacting surface. In some variations, a depth limiter may comprise a flat wire that may help to provide resistance to forward travel while reducing the likelihood of cutting through the tissue surface.

Figure 3D:
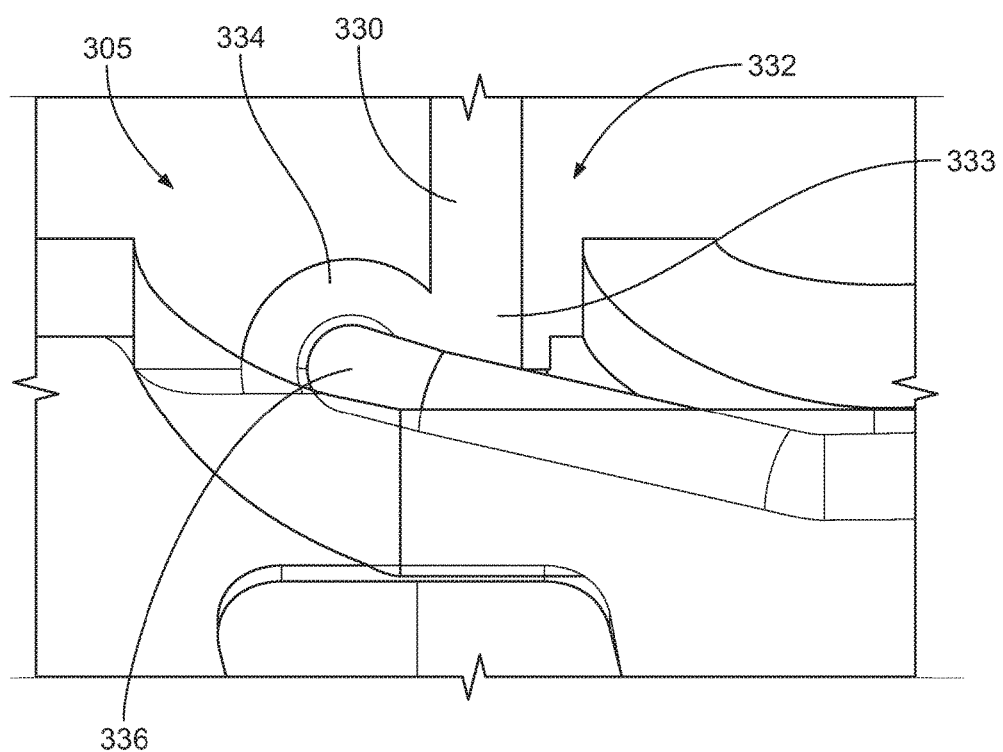
FIG. 3D depicts a close-up view of one variation of a rotatable attachment mechanism between the depth limiter and the elongate body of the delivery catheter.
Figure 3E:
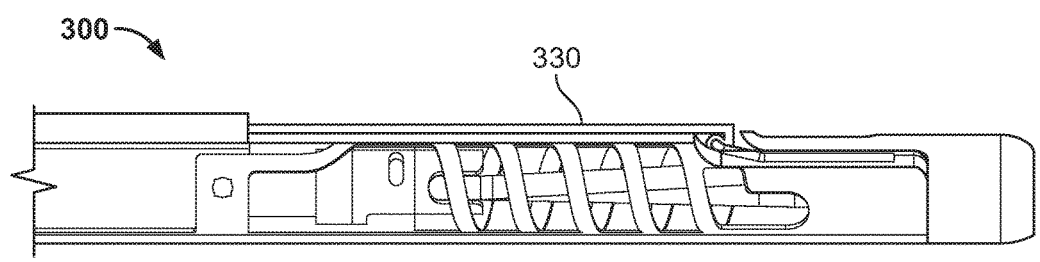
FIG. 3E is a side view of a distal portion of another variation of the anchor delivery catheter of FIG. 3A, where the tissue depth limiter is in a compressed configuration.

The distal end of the depth limiter may be attached to the elongate body of the delivery catheter by any suitable method. For example, the distal end may be attached to the elongate body (e.g., the outer surface of the elongate body)

by welding, soldering, and the like, and/or using one or more adhesives. These types of attachment mechanisms may allow the distal end of the depth limiter to be rigidly attached to the elongate body. In other variations, other types of attachment mechanisms may allow the distal end of the depth limiter to pivot, rotate, slide and/or otherwise deflect with respect to the elongate body. One variation of a rotatable attachment mechanism 332 is depicted in FIG. 3D, which is an enlarged view of the attachment of the distal end 333 of the depth limiter and the elongate body 304 depicted in FIG. 3A. In this variation, the attachment mechanism 332 may comprise a curved pin/shaft or ringed structure 336 disposed within a groove 305 of the elongate body 304. The ringed structure 336 may be a closed ring or an open ring constructed from a single component (e.g., a unibody component having a C-shape or a U-shape) or two components (e.g., two L-shaped components that are joined together). The distal end 333 of the depth limiter 330 may comprise a loop 334, which may be slidably or rotatably coupled with the ringed structure 336. In some variations, the loop may be integrally formed with the proximal portion of the depth limiter 330, while in other variations, the loop may be a hypodermic tubing that may be attached to the proximal portion of the depth limiter. For example, the loop of a depth limiter may be formed from a hypodermic tube may have an inner diameter of about 0.008 in, an outer diameter of about 0.016 in, and a wall thickness of about 0.004 in that is soldered or welded to a proximal portion of the depth limiter. The loop 334 of the depth limiter may track around the circumference of the ringed structure 336 counterclockwise or clockwise (depicted in FIG. 3C along arrows 340L and 340R, respectively). In this variation, the plane defined by the curve of the distal portion 331 may sweep between about 1 degree to about 90 degrees counterclockwise, and/or may sweep between 1 degree to about 90 degrees clockwise. The rotation or pivoting of the curved distal portion may provide a visual indication (in addition to a tactile indication) that a preselected tissue depth has been attained.

Also disclosed herein are methods of visualizing the surface of a target tissue and determining the penetration depth of an anchor delivery catheter into the target tissue. In some variations, these devices and methods may be used to deliver anchors to a particular depth in the endocardium of the left ventricle during a beating heart procedure. One example of a method for visualizing and determining the depth of delivery catheter penetration into tissue is outlined in the flow diagram of FIG. 4A and depicted in FIGS. 5A-5K. The method 400 is one in which tissue anchors are delivered to endocardium of the left ventricle (LV), though it should be appreciated that this method may be employed in many other procedures as well. Such method may comprise using fluoroscopy imaging to locate the myocardium, position the catheters, and deliver one or more tethered anchors. Fluoroscopic images or video may be taken from a short axis view of the LV or other views of the LV. FIG. 5A shows the short axis of the left side of the heart 10 with the surrounding myocardium 11, endocardium 12, LV chamber 13 and aortic outflow tract and aortic valve 14.

Figure 5A:
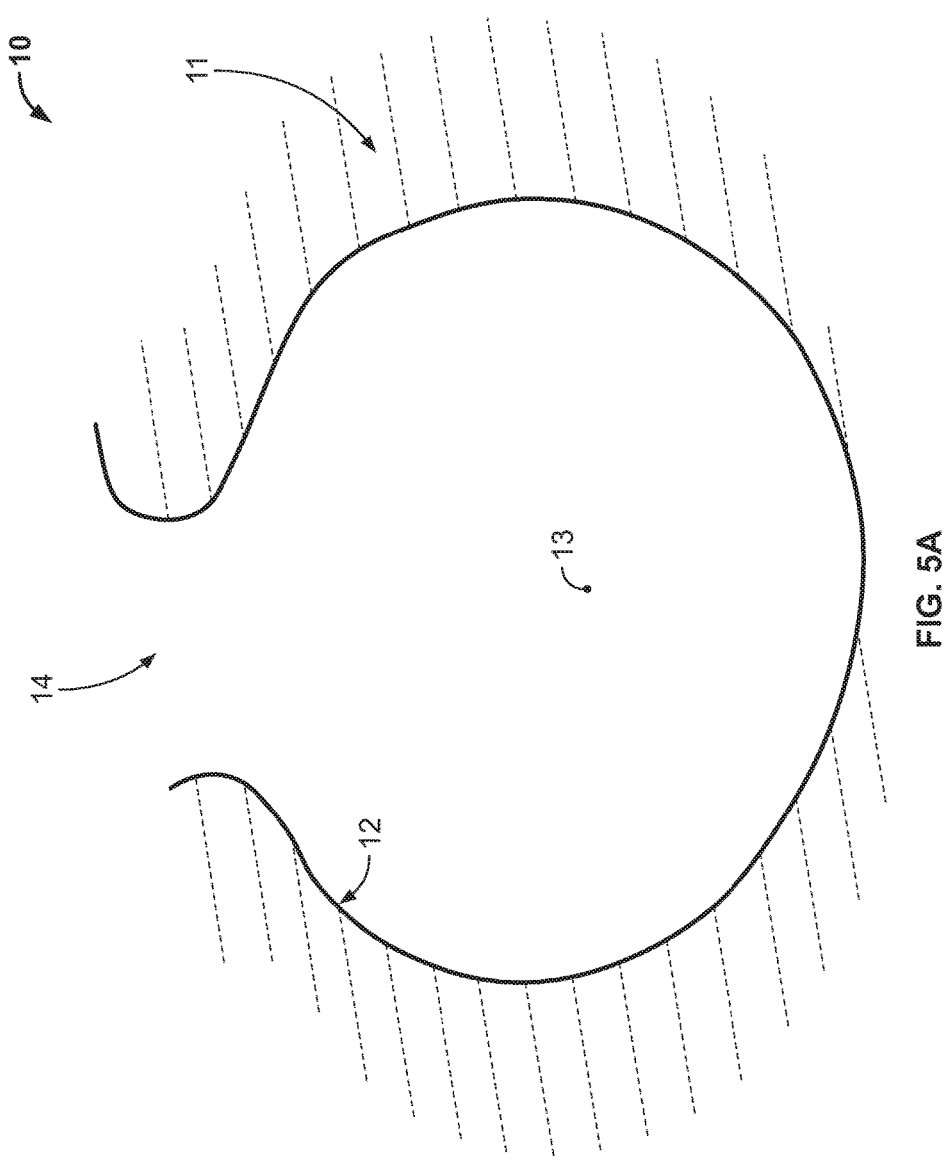
Figure 5B:
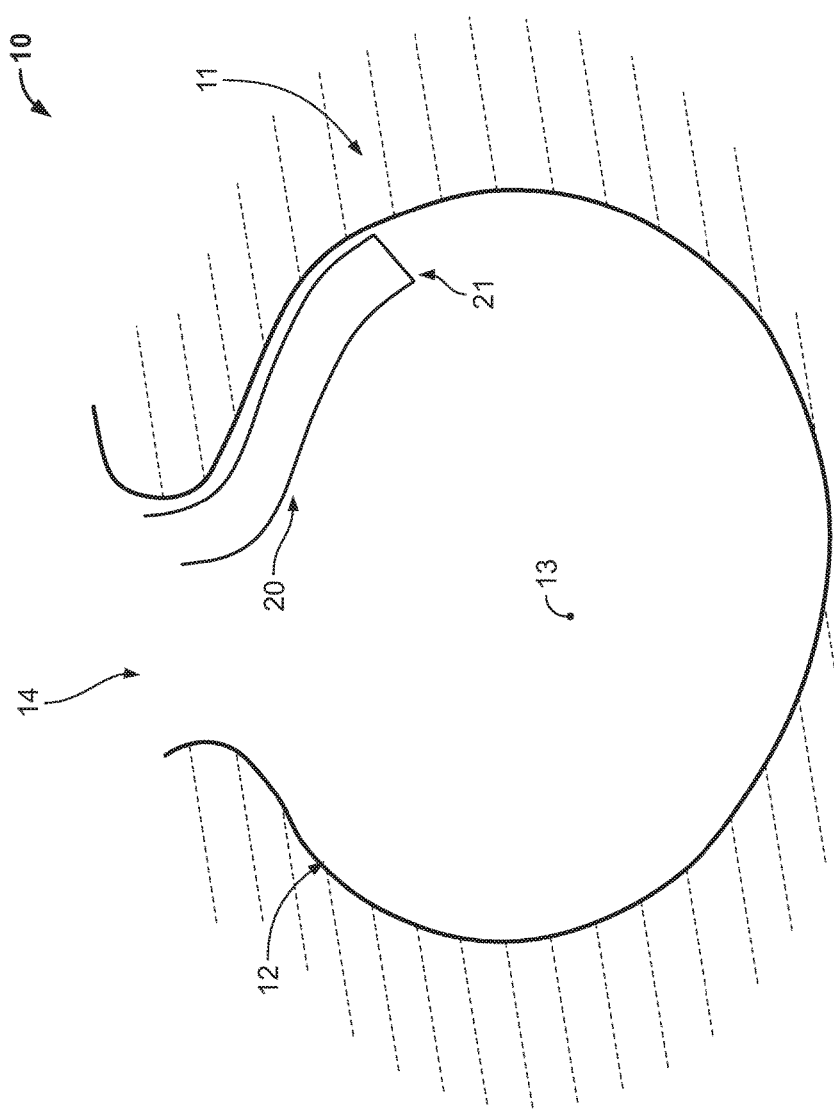
Figure 5C:
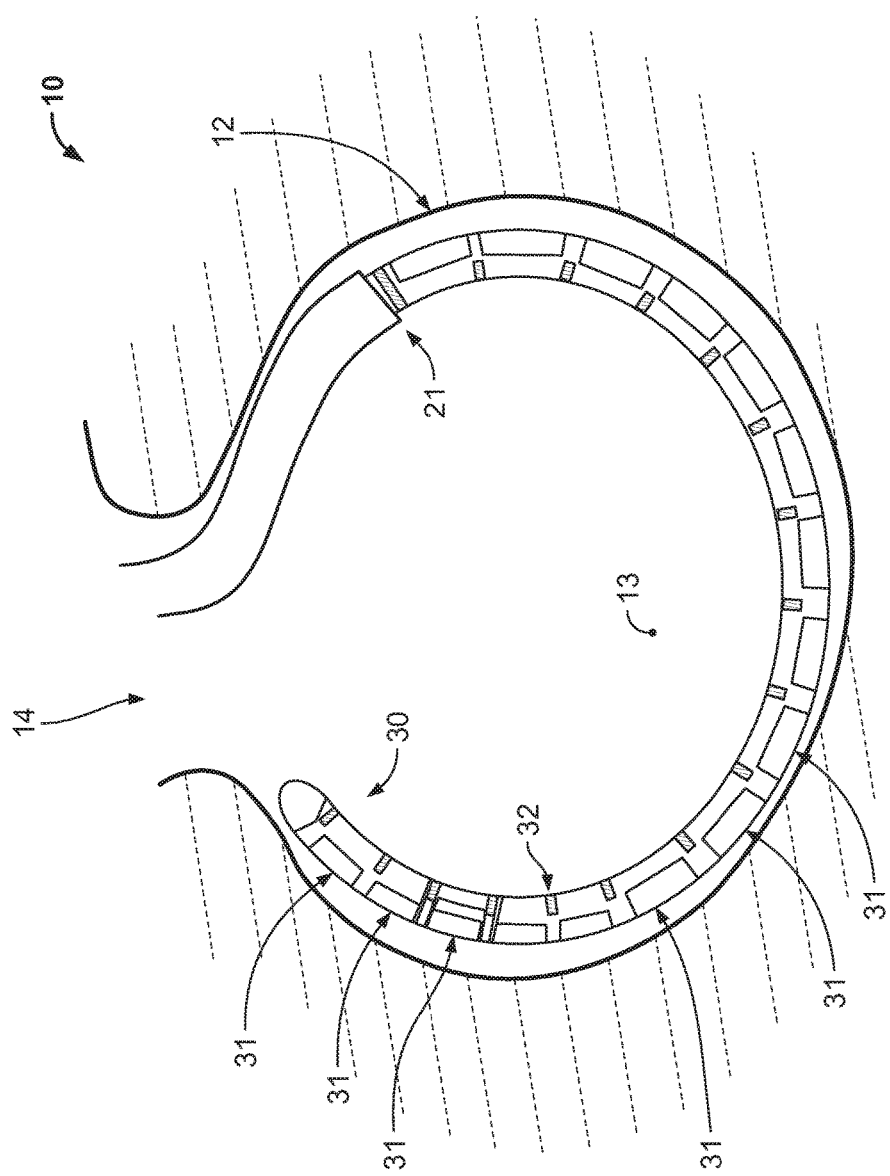
Figure 5D:
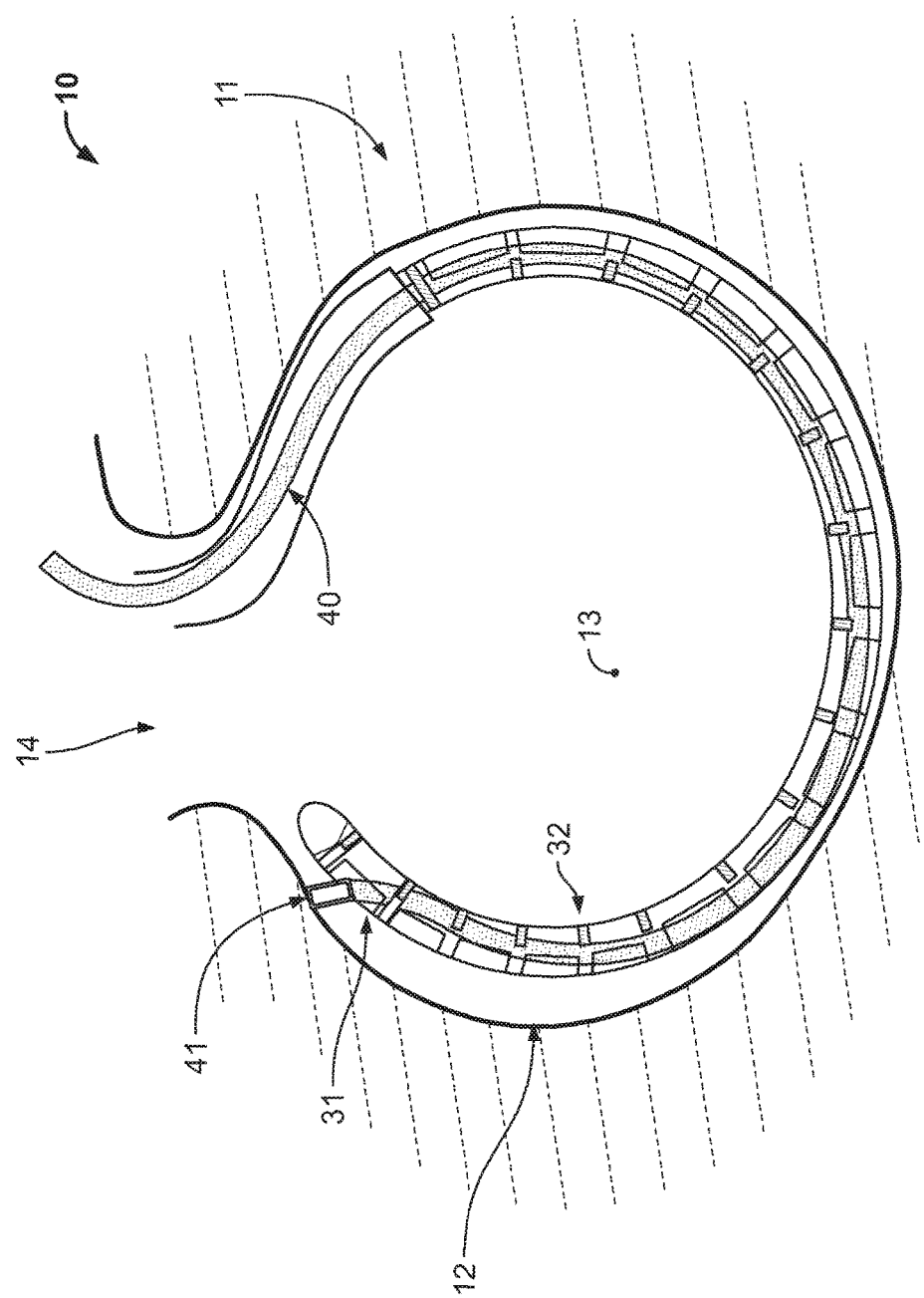
Figure 5G:
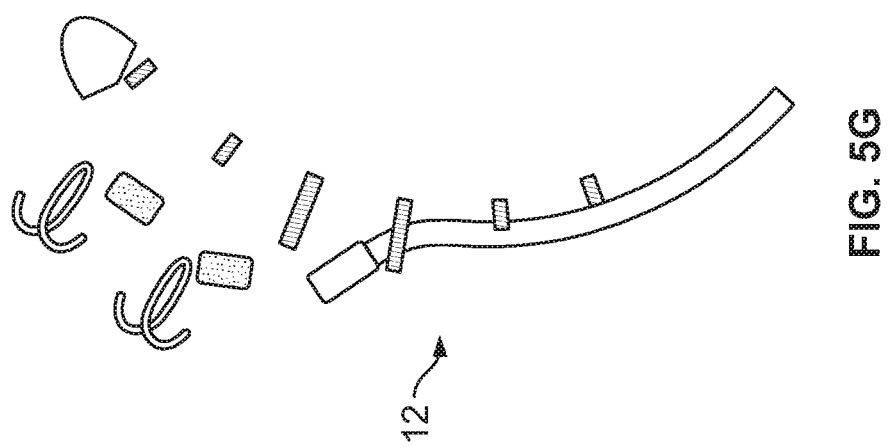

The method 400 may comprise advancing a guide catheter (step 402) to subvalvular tissue in the LV. FIG. 5B depicts a guide catheter 20 that may extend across the aortic valve (AV) and tangent to the LV wall, with a distal opening 21 that may be inserted across the aortic valve 14 and placed tangent to the endocardium 12. The method 400 may then comprise advancing a tunnel catheter through the guide catheter (step 404) such that a length of the tunnel catheter is positioned against or near the endocardium. FIG. 5C depicts placing a tunnel catheter 30 deployed from the guide catheter against or near the endocardium 12. The tunnel catheter may extend around and alongside the LV wall. Radiopaque markers and windows may be disposed along the outer radius of the tunnel catheter wall, through which delivery catheters can be deployed. For example, the tunnel catheter may be a template device, using windows 31 and radiopaque markers 32 to direct the placement of devices, such as anchors, into the myocardium of the LV. Next, the method 400 may comprise advancing a delivery catheter through the tunnel catheter (step 406) to a selected window of the tunnel catheter.

If a tissue depth indicator is not used, the method would comprise the steps depicted in FIGS. 5D-5G. As depicted there, a delivery catheter 40 may be advanced through the tunnel catheter 30 such that the distal tip 41 exits a preferred window 31 and contacts endocardium 12. Advancing delivery catheter 40 further causes it to penetrate endocardium 12 to a desired depth. FIG. 5E schematically depicts a fluoroscopic image of the guide catheter, tunnel catheter and delivery catheter positioned along endocardium of the LV. The information revealed/depicted in a fluoroscopic image is relatively sparse, especially with respect to tissue location (e.g., boundary of the myocardium surface) and depth of penetration. Specifically, there is little or no information regarding apposition between endocardium 12 and tunnel catheter 30, tenting of endocardium 12 at tip 41 of the delivery catheter 40 or trabeculations that may be present on endocardium 12 near the window 31. Even after several anchors are deployed into the endocardium, with links 60 between them that are located adjacent to endocardium 12 (as depicted in FIG. 5F), the resulting fluoroscopic image (represented in FIG. 5G) remains remarkably void of landmarks that locate the boundary of the endocardium 12, the boundary of the myocardium, and/or any other curves of structures located on the target cardiac tissue.

Figure 5H:
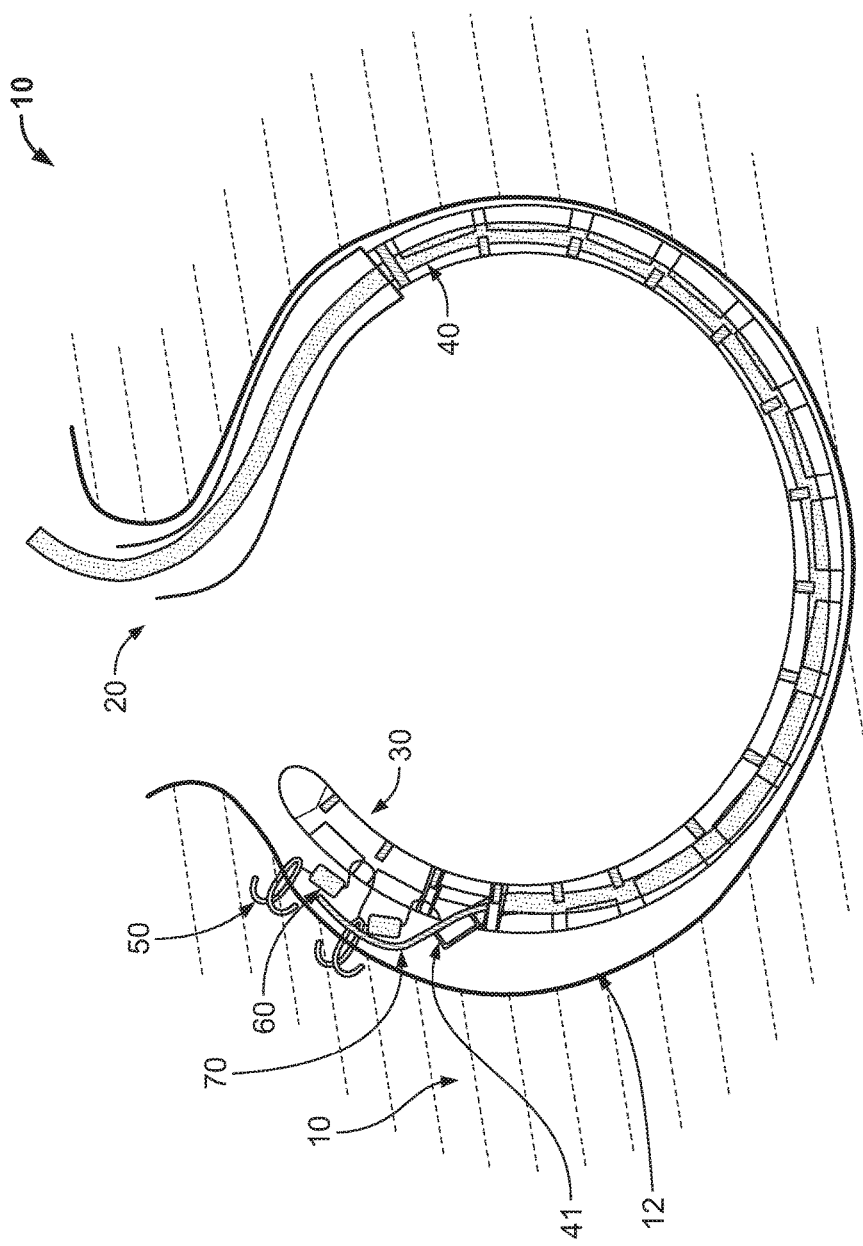
Figure 51:
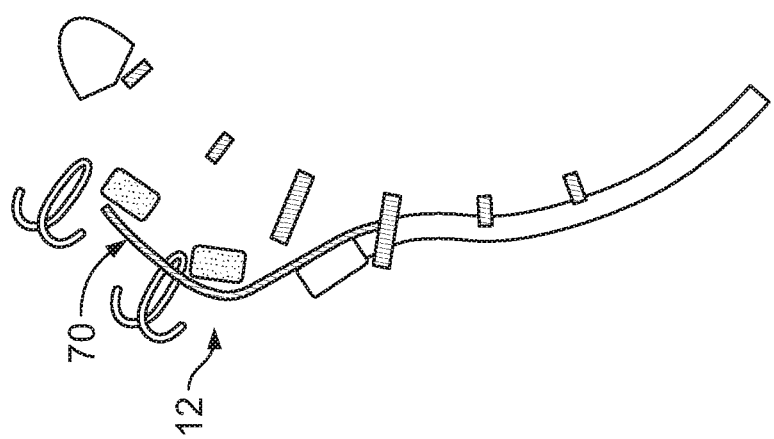
Figure 5J:
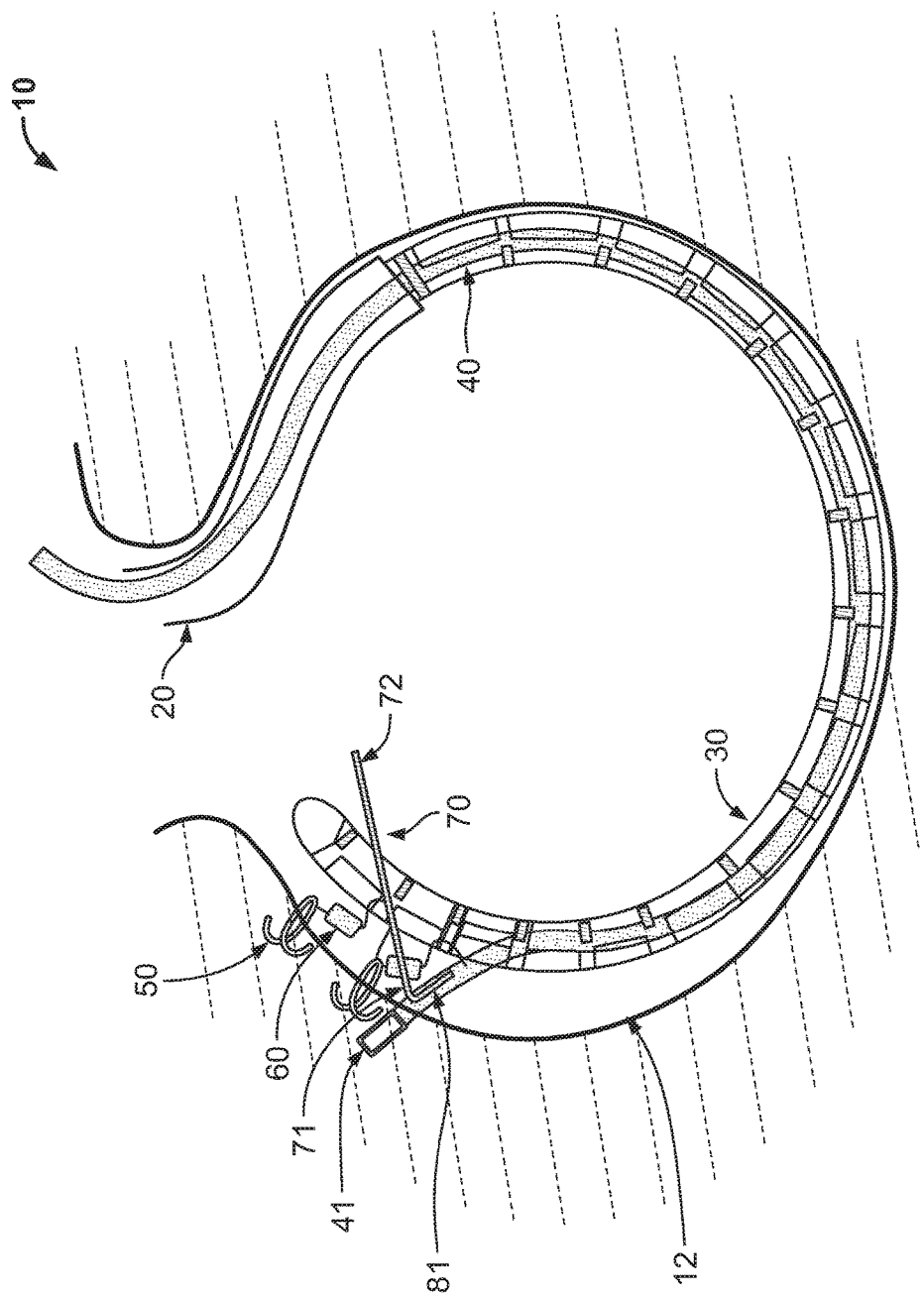
Figure 6B:
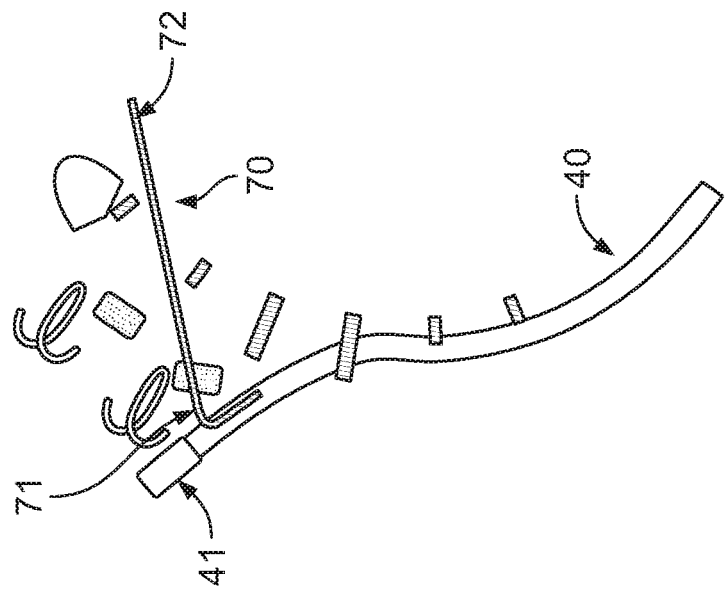
FIGS. 6A and 6B are schematic fluoroscopic depictions of a tissue depth indicator in a first configuration and a second configuration, respectively.
Figure 6A:
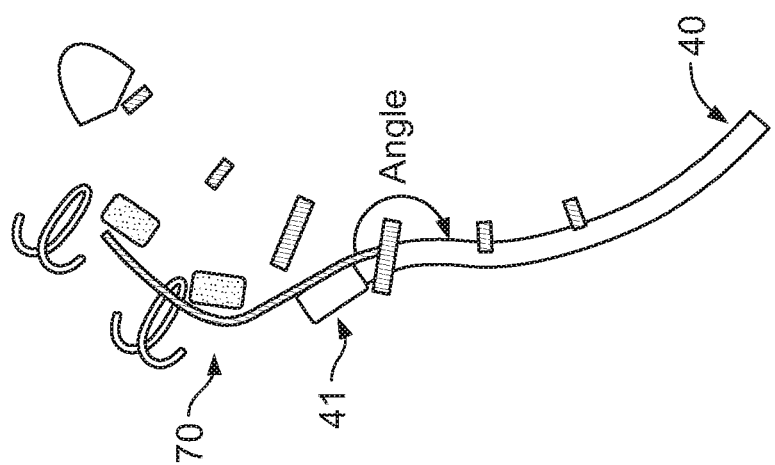

Using a delivery catheter with a tissue depth indicator may help to provide information about the location of the endocardium as well as the penetration depth of the delivery catheter tip. To continue from step 406 of the method 400, the next step may comprise advancing the tissue depth indicator out of a lumen of the delivery catheter (step 408) ahead of the distal tip of the delivery catheter, as depicted in FIG. 5H. FIG. 5H depicts a delivery catheter comprising a radiopaque depth indicator wire 70. Depth indicator wire 70 may be translatable to extend distally or proximally with respect to the distal end 41 of delivery catheter 40, though in some variations the depth indicator wire may be fixed and not translatable along the longitudinal axis of the delivery catheter. The method 400 may comprise delineating the boundary of the ventricular wall or myocardium surface using the depth indicator wire (step 410). The depth indicator wire may be in the first configuration, as described previously and also depicted in FIG. 6A. In the first configuration, the depth indicator wire may be used to interrogate the surface of endocardium 12 and may provide a durable localization and visualization of endocardium 12 where distal tip 41 penetrates. The delineation of the location and/or surface textures or structures by the deflections and curves of the depth indicator wire may be evident in the resulting fluoroscopic image (FIG. 5I). This may facilitate the identification of the location of endocardium 12. The method 400 may then comprise advancing the delivery catheter such that the distal tip of the delivery catheter penetrates through the endocardium and into the myocardium (step 412). When a desired and/or preselected penetration depth is attained, the depth indicator wire may transition to the second configuration. That is, an inflection or discontinuity may be introduced in the depth indicator wire resulting from the tissue pushing on the depth indicator wire, thereby deflecting the distal portion of the wire away from the tissue surface. FIGS. 5J and 6B schematically depict the distal segment 81 of the lumen in which depth indicator wire 70, and its location relative to distal tip 41 of the delivery catheter 40, as well as the inflection or discontinuity 71 in the curvature of the distal portion of the indicator wire. This discontinuity 71 and the straight distal portion 72 of the indicator wire 70 may provide a clear visual signal that the desired depth of penetration below endocardium 12 has been achieved. FIG. 5K is a depiction of the fluoroscopic image of the arrangement in FIG. 5J. After the depth indicator wire has transitioned to the second configuration and the inflection or discontinuity is identified, the practitioner may stop advancing the delivery catheter into the endocardium (step 414) and deliver the anchor into the endocardium (step 416). In some variations, all of the anchors may be delivered with the guidance provided by a tissue depth indicator. For example, the first and second anchors depicted in FIGS. 5D-5G may be deployed into tissue using method 400. Furthermore, fluoroscopic images may be acquired at any point during method 400, from any view (e.g., short axis view (SAX), long axis view (LAX), A/P view, oblique views, etc.).

Although the method 400 uses the anchor delivery catheter with additional catheters (e.g., a guide catheter and a tunnel catheter), it should be understood that the anchor delivery catheter may be used to deliver anchors without other catheters, with fewer catheter, or with more catheters. One example of a method for delivering anchors is depicted in FIG. 4B. The method 420 may comprise advancing a delivery catheter to the surface of the target tissue (step 422), advancing the depth indicator out of a lumen of the delivery catheter ahead of the distal tip of the delivery catheter (step 424), delineating the boundary of the surface of the target tissue using the depth indicator (step 426), and advancing the delivery catheter to penetrate the target tissue (step 428) until a desired penetration depth is reached. The method 420 may then comprise stopping the advancement of the delivery catheter when the distal portion of the depth indicator deflects away from the surface of the target tissue (i.e., transitions from the first configuration to the second configuration, which has an inflection or discontinuity) and delivering the anchor into the tissue at the preselected depth. Furthermore, fluoroscopic images may be acquired at any point during method 420, from any view.

Figure 4A:
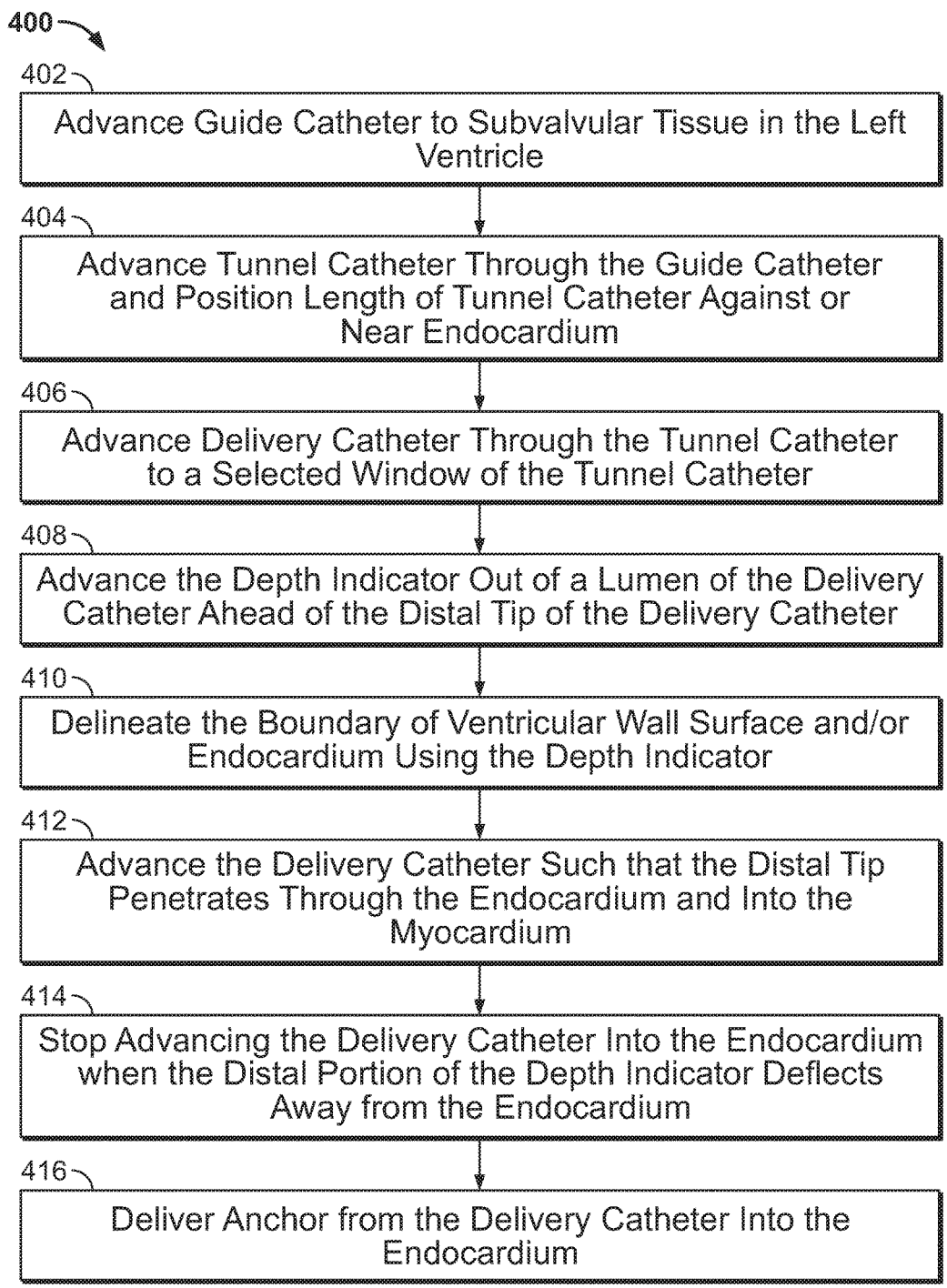
FIG. 4A is a flowchart depiction of one variation of a method for delivering anchors using a delivery catheter comprising a depth indicator.
Figure 4B:
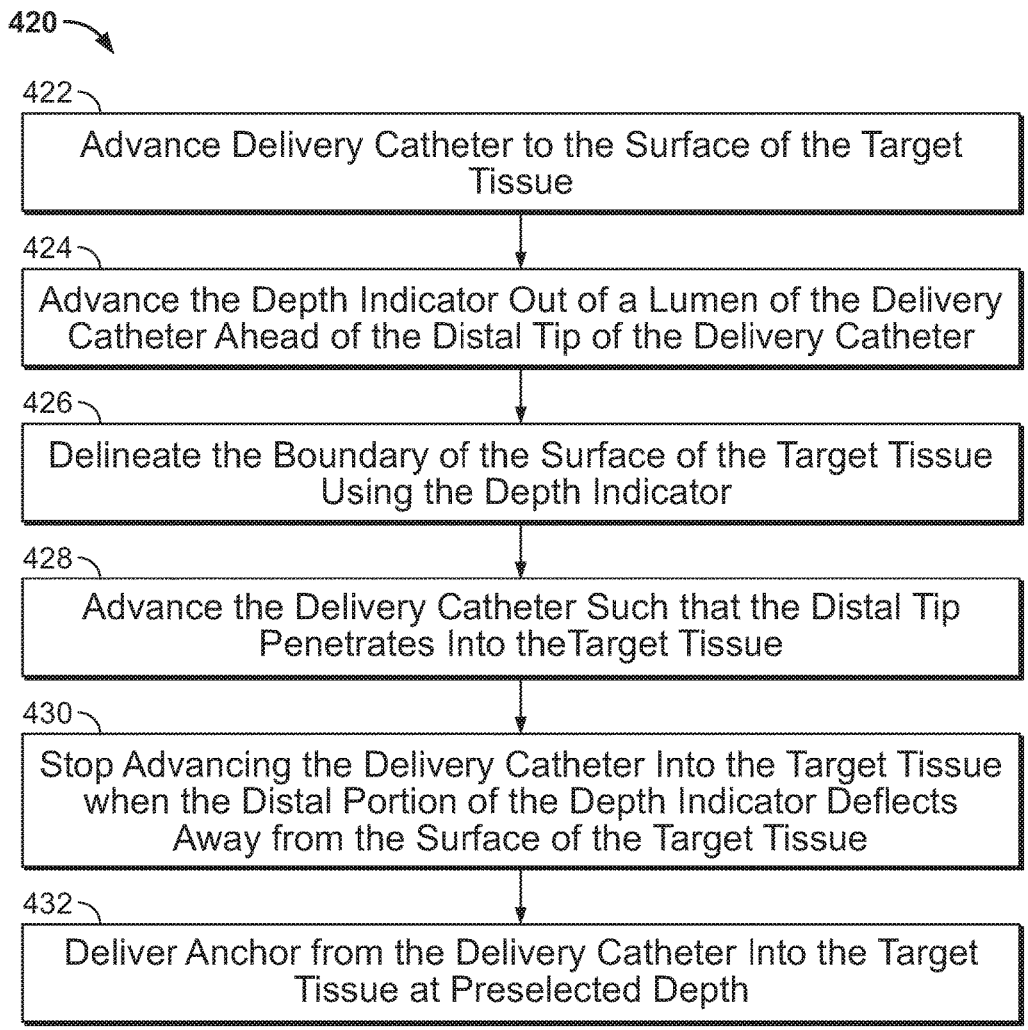
FIG. 4B is a flowchart depiction of another variation of method for delivering anchors using a delivery catheter comprising a depth indicator.

An anchor delivery catheter comprising a tissue depth limiter may also be used to perform the methods of FIGS. 4A and 4B. However, the tissue depth limiter may not be capable of delineating the boundary of the surface of the target tissue. Instead, prior to contacting the tissue, the depth limiter may be transitioned from the first collapsed configuration to the second expanded configuration. In the expanded configuration, the depth limiter may provide a tactile signal that the tip of the delivery catheter has attained a preselected or maximum penetration depth. Optionally, an anchor delivery catheter comprising a tissue depth limiter that has a distal end rotatably attached to the elongate body of the delivery catheter may provide a visual cue that the preselected penetration depth has been attained. For example, the rotation of the depth limiter when it abuts the target tissue surface may provide a visual change in a fluoroscopic image that indicates a desired or maximum penetration depth has been attained. Furthermore, fluoroscopic images may be acquired at any point during these procedures, from any view.

Also disclosed herein are kits comprising an anchor delivery catheter and a tissue depth indicator and/or tissue depth limiter. In one variation, a kit may comprise an anchor delivery catheter comprising an elongate body with a first longitudinal lumen terminating at a first distal opening and a second longitudinal lumen terminating at a second distal opening. The kit may further comprise a depth indicator wire configured to be disposed within the second longitudinal lumen of the elongate body, where the depth indicator wire may have a proximal portion and a distal portion that is relatively more compliant or flexible than the proximal portion. The depth indicator wire may be pre-assembled during manufacturing so that it is disposed within the second longitudinal lumen, or may be kept separate from the elongate body and inserted by the practitioner just prior to use. Optionally, the kit may comprise an anchor disposed within the first longitudinal lumen. In another variation, a kit may comprise an anchor delivery catheter comprising an elongate body with a first longitudinal lumen terminating at a first distal opening and a second longitudinal lumen terminating at a second distal opening, and an anchor disposed within the first longitudinal lumen. The tissue depth indicator may be in a separate kit. Alternatively, a kit may comprise an anchor delivery catheter comprising an elongate body with a first longitudinal lumen terminating at a first distal opening and a second longitudinal lumen terminating at a second distal opening and a tissue depth limiter disposed within the second longitudinal lumen and attached at a distal end of the elongate body. The kit may or may not include an anchor disposed within the first longitudinal lumen.

The invention claimed is:

1. A tissue anchor delivery device comprising:
    an elongate body having a longitudinal axis and comprising a proximal end, a distal end, a first longitudinal lumen that terminates at a first distal opening located at the distal end of the elongate body, and a second longitudinal lumen that terminates at a second distal opening located proximal to the distal end of the elongate body, wherein a longitudinal distance between the first distal opening and the second distal opening corresponds to a pre-selected tissue anchor delivery depth;
    a tissue anchor coupled to a tether disposed in the first longitudinal lumen and configured to exit the first distal opening when deployed into tissue, wherein the tether is coupled to an eyelet of the tissue anchor; and
    a tissue depth indicator extendable from the second distal opening
    wherein a distal portion of the tissue depth indicator extends out from the second distal opening and comprises a first configuration wherein the distal portion extends toward the distal end of the elongate body and a second configuration wherein the distal portion extends away from the distal end of the elongate body, and wherein the tissue depth indicator is configured to transition from the first configuration to the second configuration after the distal end of the elongate body has penetrated a tissue surface at the pre-selected anchor delivery depth, and
    wherein the tissue depth indicator comprises a radiopaque indicator wire having a proximal portion, and wherein the distal portion of the indicator wire is more compliant than the proximal portion.

2. The delivery device of claim 1, wherein the distal portion has a length from about 1 cm to about 5 cm.

3. The delivery device of claim 2, wherein the distal portion has a length of about 3 cm.

4. The delivery device of claim 1, wherein the distal portion of the tissue depth indicator extends beyond the distal end of the elongate body.

5. The delivery device of claim 1, wherein in the first configuration, the distal portion of the indicator wire forms an obtuse angle with respect to the second longitudinal lumen, and in the second configuration, the distal portion of the indicator wire forms an acute angle with respect to the second longitudinal lumen.

6. The delivery device of claim 1, wherein in the first configuration, sliding the tissue depth indicator within the second longitudinal lumen varies the length of the distal portion of the indicator that exits the second longitudinal lumen.

7. The delivery device of claim 6, wherein the obtuse angle is about 120 degrees and the acute angle is about 80 degrees.

8. The delivery device of claim 1, wherein in the first configuration, sliding the tissue depth indicator within the second longitudinal lumen varies the length of the distal portion of the indicator that exits the second longitudinal lumen.

9. The delivery device of claim 1, wherein at least the distal portion of the indicator wire is radiopaque.

10. The delivery device of claim 1, wherein the proximal portion of the indicator wire has a first stiffness and the distal portion of the indicator wire has a second stiffness, wherein the second stiffness is about 5% to about 50% of the first stiffness.

11. The delivery device of claim 1, wherein the first longitudinal lumen is distinct from the second longitudinal lumen.

12. The delivery device of claim 11, wherein the first longitudinal lumen and the second longitudinal lumen are separated by a wall.

13. The delivery device of claim 1, further comprising a push member slidably disposed within the first longitudinal lumen and configured to contact and distally advance the tissue anchor, and a stop structure located within the first longitudinal lumen and configured to restrict sliding the push member past a selected location along the first longitudinal lumen.

14. The delivery device of claim 1, wherein the distal portion of the tissue depth indicator extends along a longitudinal length of the elongate body between the first distal opening and the second distal opening in the first configuration, and the tissue depth indicator deflects away from the longitudinal length of the elongate body in the second configuration.

* * * * *